(12) United States Patent
Ziehl et al.

(10) Patent No.: US 12,422,407 B2
(45) Date of Patent: Sep. 23, 2025

(54) SHORT-TERM AE MONITORING TO IDENTIFYING ASR PROGRESSION IN CONCRETE STRUCTURES

(71) Applicant: University of South Carolina, Columbia, SC (US)

(72) Inventors: Paul Ziehl, Irmo, SC (US); Vafa Soltangharaei, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 17/860,171

(22) Filed: Jul. 8, 2022

(65) Prior Publication Data

US 2023/0087465 A1 Mar. 23, 2023

Related U.S. Application Data

(60) Provisional application No. 63/242,635, filed on Sep. 10, 2021.

(51) Int. Cl.
| | | |
|---|---|---|
| *G01N 29/06* | (2006.01) | |
| *G01N 29/12* | (2006.01) | |
| *G01N 29/14* | (2006.01) | |
| *G01N 33/38* | (2006.01) | |

(52) U.S. Cl.
CPC ......... *G01N 29/0654* (2013.01); *G01N 29/12* (2013.01); *G01N 29/14* (2013.01); *G01N 33/383* (2013.01)

(58) Field of Classification Search
CPC .... G01N 29/0654; G01N 29/12; G01N 29/14; G01N 33/383; G01N 2291/106; G01N 29/4481; G01N 29/46; G01N 2291/0258
See application file for complete search history.

(56) References Cited

U.S. PATENT DOCUMENTS

| | | | |
|---|---|---|---|
| 2014/0379304 A1* | 12/2014 | Anderson | G01N 29/46 |
| | | | 702/190 |
| 2016/0209372 A1* | 7/2016 | Ziehl | G01N 29/46 |
| 2020/0166909 A1* | 5/2020 | Noone | G06N 20/00 |
| 2021/0304895 A1* | 9/2021 | Buscemi | G06N 20/20 |

OTHER PUBLICATIONS

"A generalizable deep learning framework for localizing and characterizing acoustic emission sources in riveted metallic panels" by Ebrahimkhanlou et al. (Year: 2019).*

* cited by examiner

*Primary Examiner* — Xin Y Zhong
(74) *Attorney, Agent, or Firm* — Offit Kurman; Douglas L. Lineberry

(57) ABSTRACT

Described herein are systems and methods based on acoustic emission (AE) technology to monitor a concrete structure for a short interval and, based on signals acquired, estimate Alkali-silica reaction (ASR) progression status in the structure remotely and efficiently without halting any serviceability and operational activities of the structure, knowing the ASR progression status of the structure helps determine rehabilitation and future structural safety and serviceability of the structure.

18 Claims, 39 Drawing Sheets

(a) Concrete specimen (b) Reinforcement detail

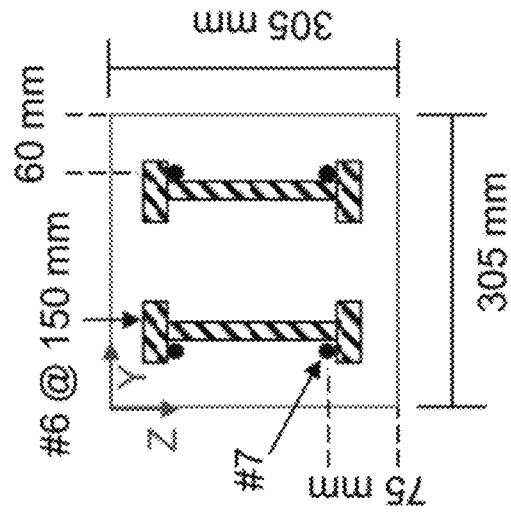
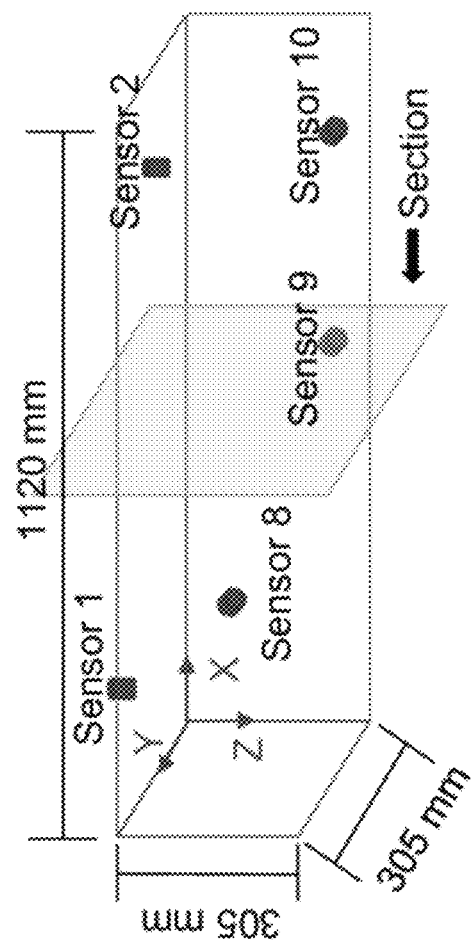
(b) Reinforcement detail
(a) Concrete specimen
FIG. 1

Table 1. Accuracies of CNN and stacked autoencoder

| Models | Accuracy |
|---|---|
| Stacked autoencoder (all signals) | 72.6% |
| Stacked autoencoder (signals from a single sensor) | 80.2% |
| CNN (all signals) | 76.7% |
| CNN (signals from a single sensor) | 85.2% |

FIG. 13

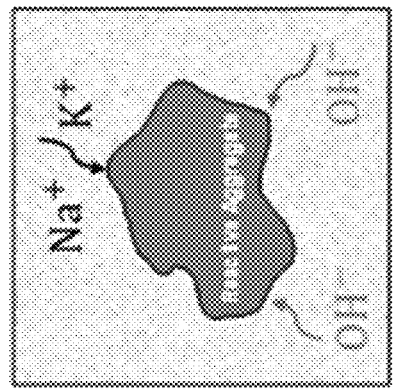
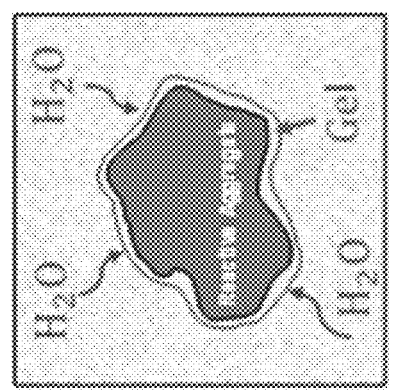
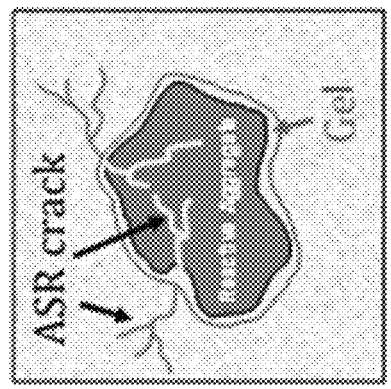
FIG. 14

Table 2. Concrete mixture proportions.

| Mixture components | Quantity (kg/m$^3$) |
|---|---|
| Cement | 350 |
| w/c ratio | 0.5 |
| Reactive coarse aggregate | 1050 |
| Nonreactive sand | 851 |
| NaOH solution (50% w/w) | 9.22 |

*FIG. 16*

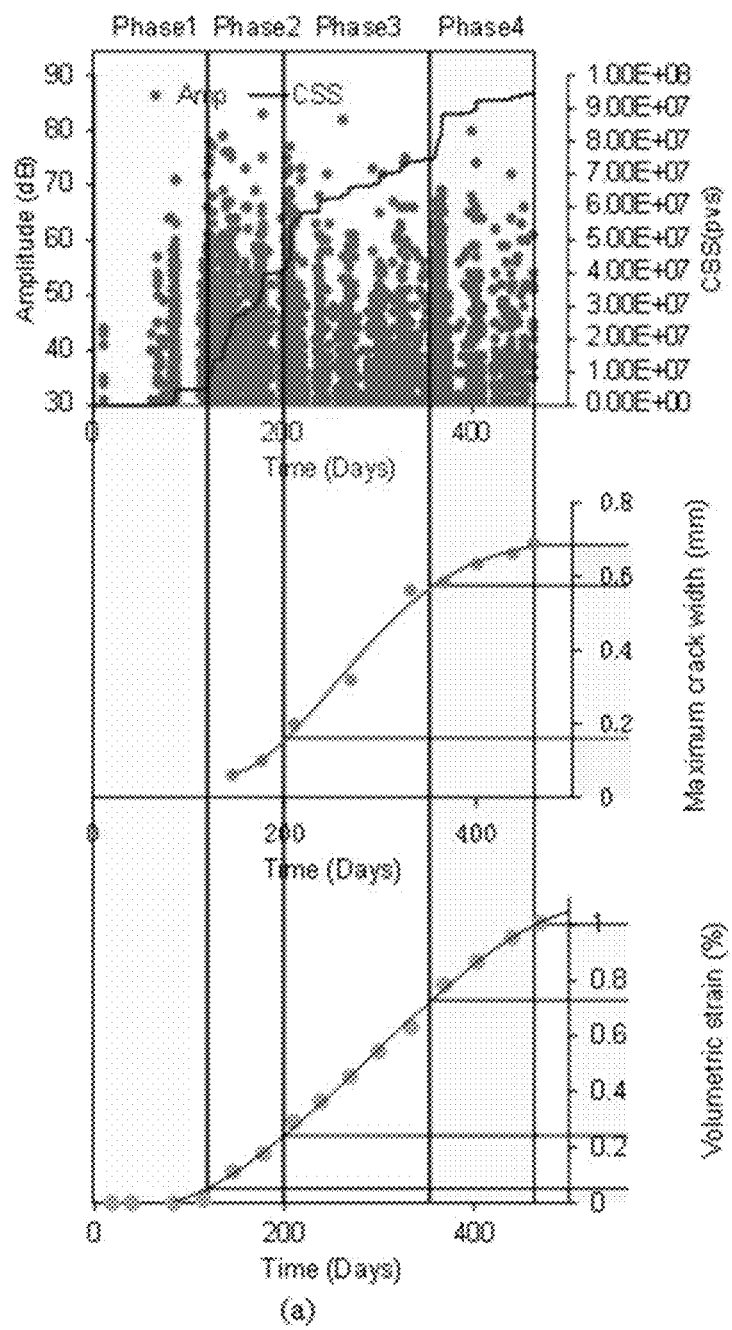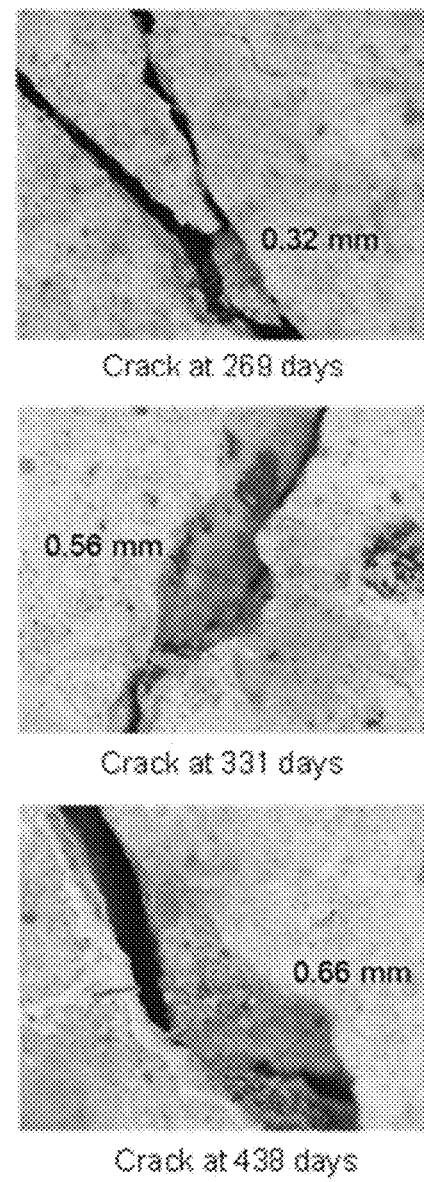
FIG. 23

Table 3. Descriptions of the AE parametric features

| Parametric features | Feature descriptions |
|---|---|
| Amplitude (dB) | The peak amplitude of AE waveform |
| Energy (arbitrary units = $10^{-14}V^2 \cdot s$) | The measure of the electrical energy measured for an AE signal |
| Count | The number of threshold crossings |
| Counts to peak (PCNTS) | The number of threshold crossings from the first crossing to the peak |
| Rise time (μs) | The time interval between first threshold crossing and peak |
| Duration (μs) | The time between the first and last threshold crossing |
| Average frequency (Hz) | Counts divided by duration |
| Frequency centroid (Hz) | A parameter to characterize the overall frequency content of an AE signal |
| Absolute energy (Atto-Joule) | The absolute measure of the electrical energy measured for an AE signal |
| Peak frequency (Hz) | Frequency of maximum signal contribution |
| Reverberation frequency (Hz) | Frequency after the peak |
| Initial frequency (Hz) | Frequency before the peak |
| Signal strength (pVs) | Integral of the rectified voltage signal over waveform duration |
| Root mean square (RMS) (mV) | The effective voltage with a characteristic time $T_{RMS}$ for an average ranging between 10 and 1000 ms |
| Average signal level (ASL) (dB) | The effective voltage with a characteristic time $T_{ASL}$ for an average ranging from 10 to 1000 ms |

*FIG. 24*

Table 4. Testing accuracies of the three CNN models.

| Trials | VGG-19 | GoogLeNet | ResNet-18 |
|---|---|---|---|
| Trial 1 | 80.2% | 81.4% | 84.8% |
| Trial 2 | 82.3% | 78.9% | 82.3% |
| Trial 3 | 79.4% | 84.6% | 83.7% |
| Trial 4 | 83.4% | 83.2% | 83.0% |
| Trial 5 | 76.9% | 82.3% | 80.3% |
| Average Accuracy | 80.4% | 82.1% | 82.8% |

*FIG. 29*

Table 5. Testing accuracies of the random forest.

| Model | Testing accuracy |
|---|---|
| RF with hit rate input | 82.9% |
| RF without hit rate input | 50.3% |

Table 6. Testing accuracies and computing times of all the models

| Model | Accuracy | Training time (s) | Testing time (s) |
|---|---|---|---|
| RGVF-HeteroESM-Net | 93.0% | 30111.14 | 0.97 |
| RGV-HeteroESM-Net | 89.6% | 30083.81 | 0.91 |
| ResNet-18-ESM | 87.5% | 4498.87 | 0.23 |
| GoogLeNet-ESM | 86.2% | 7641.29 | 0.27 |
| VGG-19-ESM | 84.4% | 17943.65 | 0.41 |
| RF-ESM | 85.3% | 33.17 | 0.06 |
| ResNet-18 | 82.8% | 899.77 | 0.05 |
| GoogLeNet | 82.1% | 1528.26 | 0.05 |
| VGG-19 | 80.4% | 3588.73 | 0.08 |
| RF | 82.9% | 6.63 | 0.01 |
| SVM | 63.7% | 3.39 | 0.01 |
| KNN | 57.1% | 2.47 | 0.02 |

*FIG. 37*

SHORT-TERM AE MONITORING TO IDENTIFYING ASR PROGRESSION IN CONCRETE STRUCTURES

STATEMENT REGARDING FEDERALLY SPONSORED RESEARCH

This disclosure was made with government support under FA8650-19-C-5035 awarded by the United States Air Force. This research was partially supported by the U.S. Department of Energy-Nuclear Energy. The government may have certain rights in the disclosure.

TECHNICAL FIELD

The subject matter disclosed herein is generally directed to a systems and methods based on acoustic emission (AE) technology to monitor a concrete structure for a short interval and, based on signals acquired, Alkali-silica reaction (ASR) progression status in the structure will be estimated remotely and efficiently without halting any serviceability and operational activities of the structures and knowing ASR progression status of structures helps determine rehabilitation and future structural safety and serviceability of the structures.

BACKGROUND

Concrete is an important infrastructure material which is widely applied in civil engineering structures. However, the brittle mechanical properties of concrete make it vulnerable to cracking. Alkali-silica reaction (ASR) is one of the main sources of concrete structure cracking. ASR is a chemical reaction that occurs between the silica in the reactive aggregate and the alkaline substance in the cement. The product of this reaction is a hygroscopic gel, which can absorb humidity and expand. The gel exerts pressure on the aggregate and cement matrix, causing cracks to form. The common structures which are exposed to ASR are bridges, concrete dams, nuclear power plants, and nuclear waste containments. Fifty-eight nuclear power plants are operating in the United States with the capacity of 800,000 MWh power generation, which is almost 20% of US electricity production. Of almost 607,380 bridges in the United States, 235,000 bridges use conventional reinforced concrete, and 108,000 bridges were constructed using prestressed concrete. There are more than 90,000 dams built in the United States, and a large portion of these dams contain concrete. The above structures are among the most important infrastructure features in the country and are exposed to degradation and cracking.

Because of the safety and radioprotection functions of concrete structures in nuclear power plants, the effects of ASR and their significance to current and long-term operation must be thoroughly addressed. The early recognition of ASR and understanding the stage of ASR progression is very vital for on-time decision making about important structures such as nuclear facilities, bridges, and dams. Understanding and detection of ASR damage are very challenging using traditional methods based on physical inspection due to hidden symptoms of ASR on the surface of structures.

Accordingly, it is an object of the present disclosure to provide a method based on acoustic emission (AE) technology to monitor a concrete structure for a short interval (14 to 20 days) and based on signals acquired, the ASR progression status in the structure will be estimated. Using the proposed method allows the owners to monitor the health of structures remotely and efficiently without halting any serviceability and operational activities of the structures. Furthermore, the method will provide the owners with information about the ASR progression status of structures, which is helpful to make a decision about rehabilitation and future structural safety and serviceability.

Citation or identification of any document in this application is not an admission that such a document is available as prior art to the present disclosure.

SUMMARY

The above objectives are accomplished according to the present disclosure by providing in one embodiment, an acoustic emission method for monitoring structural health. The method may include affixing at least one acoustic emission sensor to a structure; obtaining at least one acoustic emission waveform from the structure; employing at least one heterogeneous ensemble learning framework to analyze the at least one acoustic emission waveform to determine a condition of the structure; and wherein the method may be nondestructive to the structure being monitored. Further, the method may include converting the at least one acoustic emission waveform to at least one continuous wavelet transform image. Yet again, the method may include obtaining at least one feature based dataset by extracting at least one parametric feature from the at least one acoustic emission waveform. Still, the method may include comprising the at least one heterogeneous ensemble learning framework to include at least one convolutional neural network and at least one random forest model. Moreover, the method may include forming the convolutional neural network to comprise at least one input layer, at least one feature extraction layer, and at least one fully connected layer. Even further, the continuous wavelet transform may be expressed as $$CWT_{(a,b)} = \frac{1}{\sqrt{|a|}} \int_{-\infty}^{\infty} x(t) \psi^* \left(\frac{t-b}{a}\right) dt.$$

Yet further, the method may include forming the at least one convolutional neural network to include multiple convolution kernels. Again further, the method may include forming the multiple convolution kernels to vary in size from one another. Still yet further, the method may include detecting a fault in the structure via an increase in cumulative signal strength. Yet again, the method may include affixing the at least one sensor to an area of the structure subject to degradation.

In a further embodiment, the disclosure may provide a system for monitoring structural health. The system may include at least one acoustic emission sensor affixed to a structure for obtaining at least one acoustic emission waveform from the structure, at least one heterogeneous ensemble learning framework to analyze the at least one acoustic emission waveform to determine a condition of the structure, and the system may be nondestructive to the structure being monitored. Still further, the system may include converting the at least one acoustic emission waveform to at least one continuous wavelet transform image. Yet still, the system may include obtaining at least one feature based dataset by extracting at least one parametric feature from the at least one acoustic emission waveform. Further again, the system may include the at least one heterogeneous ensemble learning framework including at least one convolutional neural network and at least one random forest model. Still further, the system may include the convolutional neural network comprising at least one input layer, at least one feature extraction layer, and at least one fully connected layer. Moreover, the system may include that the continuous wavelet transform may be expressed as $$CWT_{(a,b)} = \frac{1}{\sqrt{|a|}} \int_{-\infty}^{\infty} x(t)\psi^*\left(\frac{t-b}{a}\right)dt.$$

Even further, the system may include the at least one convolutional neural network comprising multiple convolution kernels. Yet still further, the system may include the multiple convolution kernels varying in size from one another. Further again, the system may include detecting a fault in the structure via an increase in cumulative signal strength acquired by the at least one acoustic emission sensor. Yet again, the at least one sensor may be affixed to an area of the structure subject to degradation.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 1 shows structural details of a specimen of the current disclosure at (a) a concrete specimen and (b) reinforcement detail.

FIG. 13 shows Table 1—Accuracies of CNN and stacked autoencoder.

FIG. 14 shows that mechanism of the ASR in concrete at: (a) alkali cement react with reactive aggregates; (b) ASR gels forms around the aggregate and absorb water; and (c) ASR gels expansion and crack initiation.

FIG. 16 shows Table 2—Concrete Mixture Proportions.

FIG. 23 shows ASR phase definition at: (a) CSS of AE, crack width, and volumetric strain; (b) microscopic photos of cracks.

FIG. 24 shows Table 3-Descriptions of the AE parametric features.

FIG. 29 shows Table 4-Testing accuracies of the three CNN models.

FIG. 35 shows Table 5—The confusion matrix of RGVF-HeteroESM-Net.

FIG. 36 shows a graph of evaluation output compared to actual label.

FIG. 37 shows Table 6—Testing accuracies and computing times of all the models.

Figure 2:
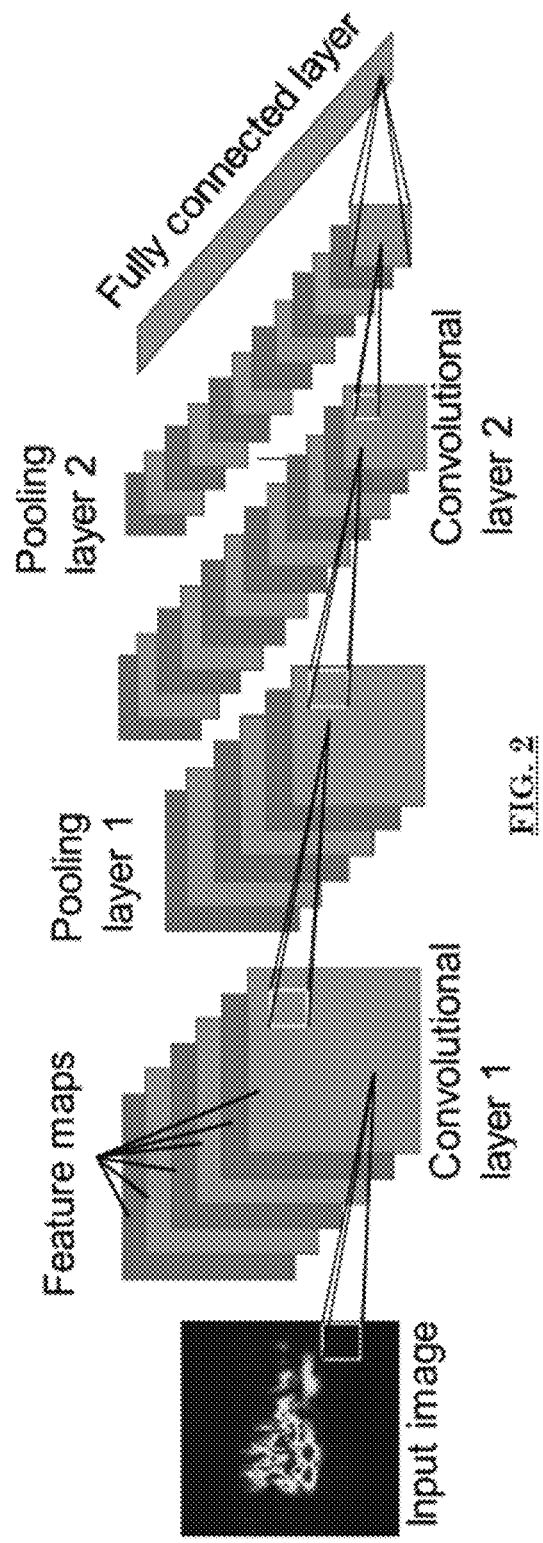
FIG. 2 shows one embodiment of an architecture of a typical CNN.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of less than x', less than y', and less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the (AE) technology methods and systems to monitor a concrete structure and acquiring Alkali-silica reaction (ASR) progression status can be presented as a combination kit. As used herein, the terms "combination kit" or "kit of parts" refers to the devices, methods, systems and any additional components that are used to package, sell, market, deliver, and/or provide the systems or methods for use. Such additional components include, but are not limited to, packaging, sensors, frequency generators, blister packages, and the like. When one or more of the systems or methods described herein or a combination thereof contained in the kit are administered simultaneously, the combination kit can contain the necessary aspects for performing the method or erecting the system. When the methods and systems are not provided simultaneously, e.g., intermittent testing or analysis, the combination kit can contain the necessary elements for the method or system in separate packaging and/or kits. The separate kit components can be contained in a single package or in separate packages within the kit.

In some embodiments, the combination kit also includes instructions printed on or otherwise contained in a tangible medium of expression. The instructions can provide information regarding the methods and systems, safety information, instructions for analysis evaluation, etc.

The present disclosure provides methods and systems to monitor structures and determine the percentage of concrete degradation (cracking) present in same. When concrete cracks, vibration waves are emitted from cracking. We record these waves and estimate the status of cracking of structures. The current disclosure helps the owners of structures obtain information about the structural health and degradation levels without stopping serviceability and structural operation. It also helps make an on-time decision about potential rehabilitation of structures, structure safety, and future serviceability. Certain aspects of the disclosure include:

Monitoring and condition assessment of structures remotely without stopping the business and services associated with the structures.

Minimizing human error in the condition assessment process by removing judgment based on visual inspections.

Increasing the efficiency of condition assessment, especially in the earlier stage of condition assessment, when the resulted defects do not appear on the surface of structures.

Increased speed and reduced cost of evaluation by automatizing a detection system, minimizing the fieldwork, and removing elements such as a petrography analysis, which takes time.

A nondestructive method that can be easily employed in structures to help prevent further damage to same.

Alkali-silica reaction (ASR) is one of the main causes of damage in concrete structures, such as nuclear power plants, which may endanger their serviceability and integrity. Acoustic emission (AE) is a passive non-destructive method for structural health monitoring. It is very sensitive and has the capability of monitoring the structure continuously. This method may prove to be an alternative for early damage detection in concrete nuclear structures affected by ASR. The innovation of this disclosure lies in the implementation of deep learning algorithms to evaluate the ASR progress.

ASR was monitored by acoustic emission in a concrete specimen which was cast with reactive coarse aggregates and reinforced by steel rebar. The AE signals recorded during the experiment were filtered and divided into two classes. Two deep learning algorithms of convolutional neural network (CNN), and stacked autoencoder were employed to classify the AE signals into the corresponding classes. The model based on CNN resulted in a classifier with a higher accuracy than the model based on the autoencoder network.

Many approaches have been utilized to monitor ASR damage and evaluate its effect on structures. The conventional approaches include regular-base visual inspection, coring and petrographic analysis, demountable mechanical strain gauge (DEMEC gauge), relative humidity or moisture content measurement, and crack indexing. These approaches have several disadvantages. For example, visual inspection is usually not effective for the early detection of ASR damage. Generally, due to in-plane constraints of structures, surface cracks appear in a late stage of ASR process, and the visual inspection of large-scale structures is time-consuming and prone to human error. Coring and petrographic analyses are destructive methods which are generally not suitable for sensitive structures such as nuclear power plants. Furthermore, it is difficult to evaluate the condition of the entire structure with only a few cores or samples.

Acoustic emission (AE) can be an alternative for the temporal evaluation of ASR damage in concrete structures used in nuclear facilities. This method is sensitive and has a continuous monitoring capability, see Ai, L., Greer, B., Hill, J., Soltangharaei, V., Ziehl, R. A. P. 2019. *Finite element modeling of acoustic emission in dry cask storage systems generated by cosine bell sources*. In: *AIP Conference Proceedings*. Ai, L., Soltangharaei, V., Anay, R., van Tooren, M. J., Ziehl, P. 2020. *Data-Driven Source Localization of Impact on Aircraft Control Surfaces*. In: *2020 IEEE Aerospace Conference*. Anay, R., Lane, A., Jáuregui, D. V., Weldon, B. D., Soltangharaei, V., Ziehl, P. 2020. *On-Site Acoustic-Emission Monitoring for a Prestressed Concrete BT-54 AASHTO Girder Bridge. Journal of Performance of Constructed Facilities*, 34 (3), 04020034. 2018; Assi, L., Soltangharaei, V., Anay, R., Ziehl, P., Matta, F. 2018. *Unsupervised and supervised pattern recognition of acoustic emission signals during early hydration of Portland cement paste. Cement and Concrete Research*, 103, 216-225.; Li, D., Wang, Y., Yan, W.-J., Ren, W.-X. 2020. *Acoustic emission wave classification for rail crack monitoring based on synchrosqueezed wavelet transform and multi-branch convolutional neural network. Structural Health Monitoring*, 1475921720922797.; Ono, K. 2011. Application of acoustic emission for structure diagnosis. *Diagnostyka*, 3-18.; Soltangharaei, V., Anay, R., Hayes, N. W., Assi, L., Le Pape, Y., Ma, Z. J., Ziehl, P. 2018b. *Damage mechanism evaluation of large-scale concrete structures affected by alkali-silica reaction using acoustic emission. Applied Sciences*, 8 (11), 2148.

Recently, there have been investigations conducted where AE was applied for the detection of damage and the quantification of the defects caused by ASR (Abdelrahman, M., ElBatanouny, M. K., Ziehl, P., Fasl, J., Larosche, C. J., Fraczek, J. 2015. *Classification of alkali-silica reaction damage using acoustic emission: A proof-of-concept study. Construction and Building Materials*, 95, 406-413.; Farnam, Y., Geiker, M. R., Bentz, D., Weiss, J. 2015. *Acoustic emission waveform characterization of crack origin and mode in fractured and ASR damaged concrete. Cement and Concrete Composites*, 60, 135-145.; Lokajíček, T., Přikryl, R., Šachlová, Š., Kuchařová, A. 2017. *Acoustic emission monitoring of crack formation during alkali silica reactivity accelerated mortar bar test. Engineering Geology*, 220, 175-182.; Soltangharaei, V., Anay, R., Hayes, N. W., Assi, L., Le Pape, Y., Ma, Z. J., Ziehl, P. 2018b. *Damage mechanism evaluation of large-scale concrete structures affected by alkali-silica reaction using acoustic emission. Applied Sciences*, 8 (11), 2148.; Weise, F., Voland, K., Pirskawetz, S., Meinel, D. 2012. *Innovative measurement techniques for characterising internal damage processes in concrete due to ASR*. In: *Proceedings of the International Conference on Alkali Aggregate Reaction (ICAAR)*, University of Texas, Austin, TX, USA. Farnam et al. (2015) utilized peak frequency and frequency centroid to characterize signal signatures that emanate from cracks in aggregates and cement paste. High-frequency signals were observed in the earlier stage of ASR, while the low-frequency signals appeared later in the ASR process. X-ray images helped the authors to verify their hypothesis. Lokajíček et al. (2017) utilized both ultrasonic pulse velocity and AE to monitor the damage caused by ASR. Four specimens with different aggregate reactivities were used. The selection of the appropriate features was generally based on experience and very challenging, especially for the complex data set. Therefore, an automatic approach is required to extract features directly from a raw data set and find potential patterns in a complex data set. This goal can be fulfilled by using deep learning methods.

Deep learning is one of the artificial intelligent techniques that simulate the information processing in the human brain (Goodfellow, I., Bengio, Y., Courville, A., Bengio, Y. 2016. *Deep learning* (Vol. 1): MIT press Cambridge.; Hassoun, M. H. 1995. *Fundamentals of artificial neural networks: MIT press*.). The advantage of deep learning is the ability to use raw data instead of extracted features as an input set. Therefore, there is no need for feature extraction and feature selection, which can be very challenging with complex data sets (Sadoughi, M., Downey, A., Bunge, G., Ranawat, A., Hu, C., Laflamme, S. 2018. *A deep learning-based approach for fault diagnosis of roller element bearings*.). In recent years, deep learning has been applied in AE (Ai, L., Soltangharaei, V., Anay, R., van Tooren, M. J., Ziehl, P. 2020. *Data-Driven Source Localization of Impact on Aircraft Control Surfaces*. In: *2020 IEEE Aerospace Conference*; Ebrahimkhanlou, A., Dubuc, B., Salamone, S. 2019. *A generalizable deep learning framework for localizing and characterizing acoustic emission sources in riveted metallic panels. Mechanical Systems and Signal Processing*, 130, 248-272.; Li, D., Wang, Y., Yan, W.-J., Ren, W.-X. 2020. *Acoustic emission wave classification for rail crack monitoring based on synchrosqueezed wavelet transform and multi-branch convolutional neural network. Structural Health Monitoring*, 1475921720922797.; Shevchik, S. A., Kenel, C., Leinenbach, C., Wasmer, K. 2018. *Acoustic emission for in situ quality monitoring in additive manufacturing using spectral convolutional neural networks. Additive Manufacturing*, 21, 598-604.). Ai et al. (2020) developed a passive nondestructive health monitoring system to locate impacts on an aircraft component based on AE and deep learning. An autoencoder algorithm was trained by the data and utilized as a part of the health monitoring system. Ebrahimkhanlou et al. (2019) worked on a deep learning framework based on a stacked autoencoder network to locate AE events on the metal structures. Li et al. (2020) utilized a convolutional neural network for AE wave classification to obtain a more accurate and comprehensive monitoring of rail cracks in the field. This method is typically helpful with complex cracking conditions, high-operational noise, and large data. Shevchik et al. (2018) proposed an on-site quality monitoring system for additive manufacturing by utilizing AE and spectral convolutional neural network.

The main focus of this disclosure is to relate AE data collected during the ASR process and attribute them to ASR expansion strains. CNN and autoencoder network were used to develop data-driven models and relate raw data to classes, which corresponded to strain ranges. Using this method, sensitive structures such as nuclear power plants or waste containments can be continuously monitored for ASR cracking without interrupting the structural serviceability or causing destruction to the structures. In addition, the ASR process phases can be determined using a developed data-driven model. Currently, the inventors are not aware of any publications of similar works that implement a deep learning algorithm to relate AE data to ASR expansion strains.

Test Setup and Experimental Procedure

A concrete block specimen with the dimensions of the 305 mm×305 mm×1120 mm was prepared for ASR testing. The specimen was cast with reactive coarse aggregates and reinforced by steel rebar. The geometrics of the specimen are shown in FIG. 1 at (a). The details of the reinforcements are shown in FIG. 1 at (b). The specimen had four longitudinal US #7 steel rebar and US #6 steel rebar with 150 mm spacing as transverse reinforcement. All rebar were T-headed to compensate for the short development length.

Ten AE sensors were attached on the surfaces of the specimen using grey double/bubble epoxy. The sensor layout is presented in FIG. 1 at (a). Three sensors (sensor 8-10) were attached on the surface of the front longitudinal side. Three sensors (sensor 5-7) were attached on the surface of the back longitudinal side. Two sensors (sensor 1-2) were attached on the top, while sensors 3-4 were attached on the bottom surface. The sensors were PKWDI with an operating frequency of 200-850 kHz.

A chamber with dimensions of 243 cm (width)×243 cm (length)×122 cm (height) was designed and built to accelerate the ASR process by providing high temperature and humidity. The temperature inside the chamber was kept at 37+3° C. The humidity was kept around 95%+5%. The specimen was placed on a steel carrier with wheels, which was designed and fabricated as a support for the specimen. DEMEC gauges were used for the expansion measurement along the three dimensions. The expansion was measured regularly every month. More details about the test setup and procedures can be found in (Soltangharaei et al., 2020).

Analysis Procedure

In this disclosure, two methods were proposed to evaluate ASR in concrete. One is based on continuous wavelet transforms (CWT) and CNN. The other one is based on a stacked autoencoder network. The AE signals are divided into two subsets according to the temporal evolution of signal features. Each subset of data can be attributed to an ASR expansion range. The data-driven models are developed using CNNs and stacked autoencoders to attribute the AE signals to the corresponding subsets.

Continuous Wavelet Transform

CWT is a joint time-frequency analysis method that captures the time-frequency characteristics in non-stationary signals such as AE signals (see Gou, L., Li, H., Zheng, H., Li, H., Pei, X. 2020. *Aeroengine Control System Sensor Fault Diagnosis Based on CWT and CNN. Mathematical Problems in Engineering*, 2020.). CWT has good performance in signal processing in terms of both time and frequency (see Li, D., Kuang, K. S. C., Koh, C. G. 2018. *Rail crack monitoring based on Tsallis synchrosqueezed wavelet entropy of acoustic emission signals: A field study. Structural Health Monitoring*, 17 (6), 1410-1424.). The continuous wavelet coefficients can be expressed by a scalogram image. The 2D scalogram images are the input for CNN models.

Convolutional Neural Network

CNN is a deep neural network with convolutional filters (Krizhevsky, A., Sutskever, I., Hinton, G. E. 2012. *Imagenet classification with deep convolutional neural networks*. In: *Advances in neural information processing systems*.). CNN is generally composed of three main parts: an input layer, feature extraction layers and a fully connected layer. The core part of the feature extraction layers mainly includes convolutional layers and pooling layers. The architecture of a typical CNN with two convolutional layers and two pooling layers is shown in FIG. 2.

In convolutional layer, multiple convolutional kernels are employed to filter the input and generate feature maps. The pooling layer is used for down-sampling of feature maps obtained from the previous convolutional layer (see, Sun, Y., Zhang, H., Zhao, T., Zou, Z., Shen, B., Yang, L. 2020. *A New Convolutional Neural Network With Random Forest Method for Hydrogen Sensor Fault Diagnosis. IEEE Access*, 8, 85421-85430.). If the image feature maps are directly used for classification without any processing, a great computational complexity will be generated, and the model is prone to overfitting. Therefore, a further reduction in the dimensionality of feature maps is required, which is the reason to construct the pooling layer after each convolutional layer. The fully connected layer is employed at the end of the CNN model. It converts the feature maps, resulting from the previous pooling layer, to one feature vector.

The CNN model applied in this disclosure is GoogLeNet. GoogLeNet was developed based on the LeNet model (see, Szegedy, C., Liu, W., Jia, Y., Sermanet, P., Reed, S., Anguelov, D., Rabinovich, A. 2015. *Going deeper with convolutions*. In: *Proceedings of the IEEE conference on computer vision and pattern recognition*.). The number of layers is extended up to 22. The GoogLeNet model is pre-trained by more than a million images from a subset of the ImageNet database (see, Deng, J., Dong, W., Socher, R., Li, L.-J., Li, K., Fei-Fei, L. 2009. *Imagenet: A large-scale hierarchical image database*. In: 2009 *IEEE conference on computer vision and pattern recognition*.). In this disclosure, the input data is 2D wavelet images. Before input datasets, the data is labeled and normalized. The wavelet coefficients are scaled between 0 to 1.

Stacked Autoencoder

Figure 3:
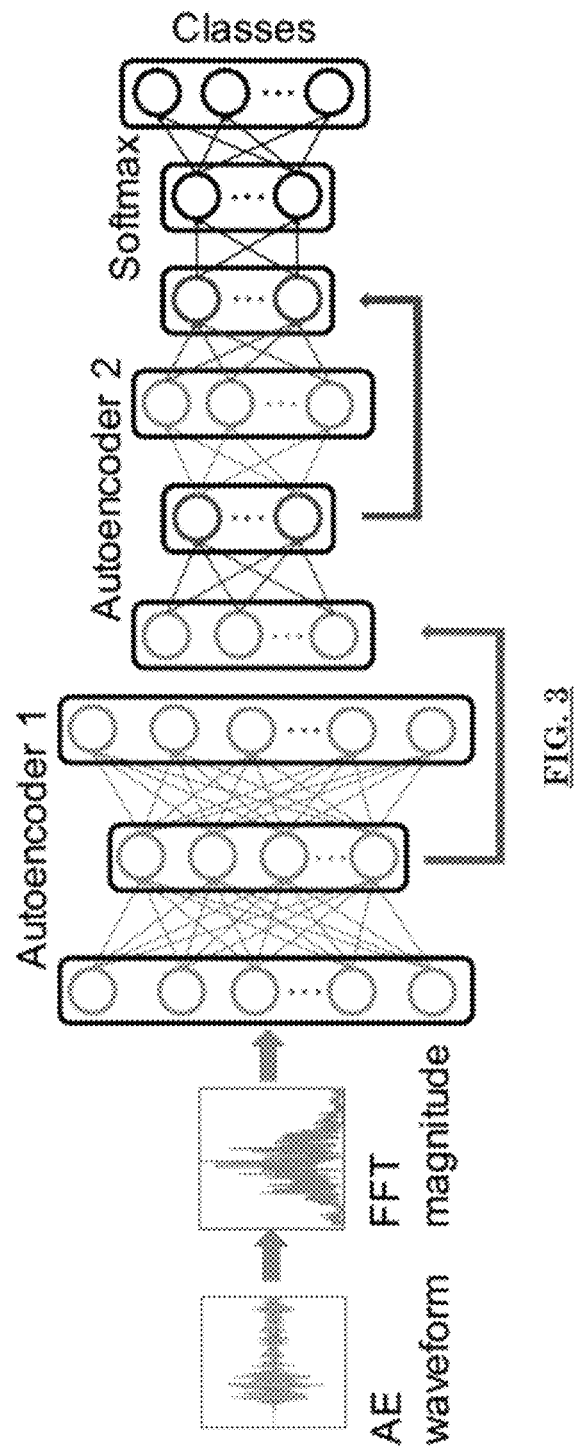
FIG. 3 a stacked autoencoder composed of two autoencoders.

The stacked autoencoder is also employed to classify the data and the results are compared to CNN. The stacked autoencoder neural network is a deep neural network composed of multiple autoencoders (see, Bengio, Y., Lamblin, P., Popovici, D., Larochelle, H. 2007. *Greedy layer-wise training of deep networks*. In: *Advances in neural information processing systems*.). An autoencoder is a neural network usually with three layers. The number of neurons in the input and output layer are kept consistent. The algorithm condenses the input data according to the dimension of the hidden layer and reconstructs the output of condensed data to the output layer (Ng and Autoencoder, 2011). An object function is designed to minimize the error in input data and output data. The compression process of input data can be considered as the feature extraction process. In stacked multiple autoencoders, more than one autoencoder is utilized to condense the data. In other words, the data is condensed several times by multiple autoencoders. A Soft-Max layer is connected to the last autoencoder to classify the final compressed features. In this disclosure a stacked autoencoder with two autoencoders is employed. The input data is the Fast Fourier Transforms (FFT) magnitude of the AE waveforms. The first and second autoencoder have a size of 100 and 50 neurons, respectively. FIG. 3 illustrates the structure of the stacked autoencoder network used in this disclosure.

Results and Discussion

Analysis of Features and Class Definition

AE data acquired from the sensors during ASR have been utilized for analyzing. Some sensors collected a large amount of extraneous data due to faulty connections and environment noise. Therefore, the first step before analyzing the AE data is filtering. The noises from faulty connections have specific signal features such as a small counts, average frequency, and peak frequency. Initially, the noises related to the faulty connections were removed by deleting the data with an average frequency lower than 60 kHz. Some faulty data remained from the first stage. Therefore, another filter was applied to the contaminated channel by removing the signals with a peak frequency of less than 80 kHz. The filtering procedure mentioned above removed a large amount of faulty data. Another procedure was then developed to further filter the data based on AE event definition. An AE event refers to a set of hits acquired by different sensors in a specific time interval, which is defined based on stress wave velocity and specimen dimensions. The events which include at least four hits were kept, and the rest of the data was filtered.

Figure 4:
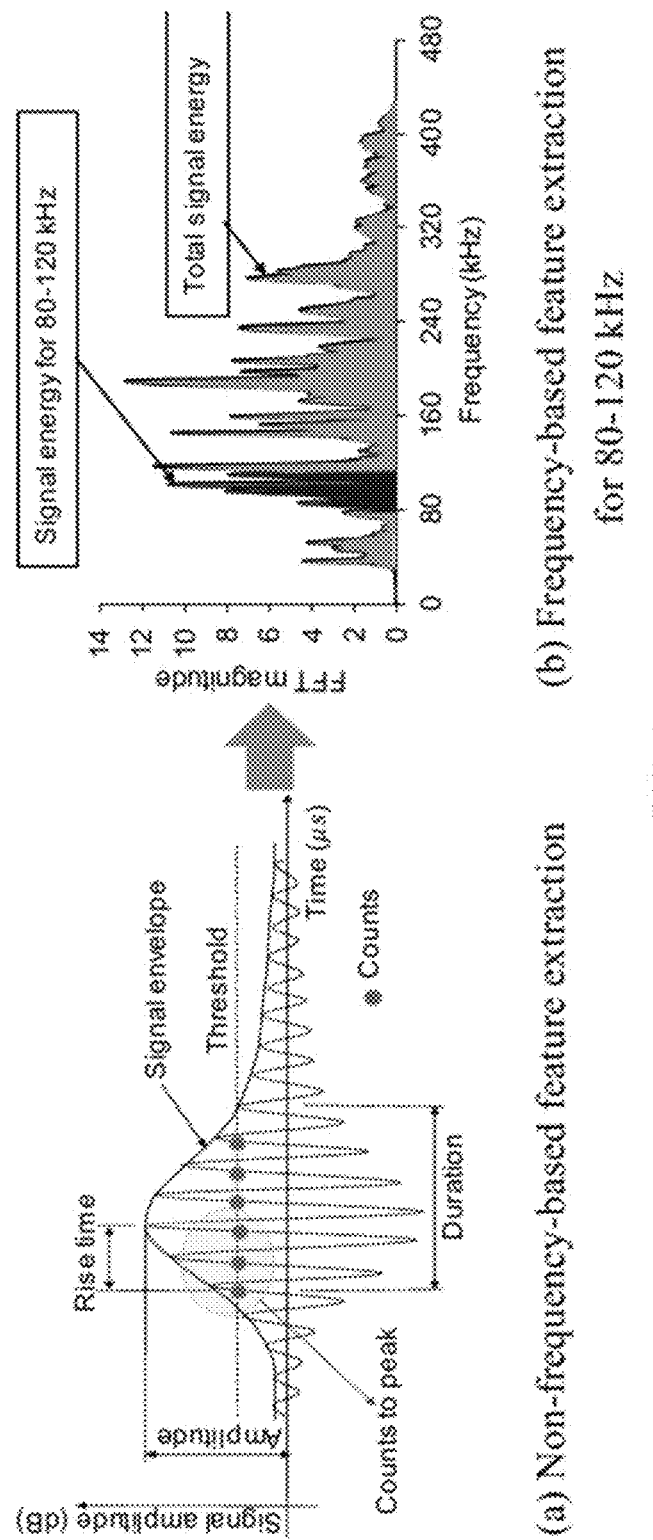
FIG. 4 shows AE features of the current disclosure at: (a) non-frequency based feature extraction; and (b) frequency-based feature extraction for 80-120 kHz.

Several AE features were extracted from the AE signals after filtering. Those features can be divided by the non-frequency-based features and the frequency-based features. The non-frequency-based features in this disclosure are counts, counts to peak, amplitude, rise time, duration, and signal strength. The non-frequency-based features are presented for a typical AE waveform as shown in FIG. 4 at (a).

To extract the frequency-based features, the AE signals were transferred to the frequency domain using FFT. The frequency domain of each signal was divided by ten equal intervals with a bandwidth of 40 kHz. The energies corresponding to each frequency band were derived by calculating the area under the FFT spectrum in that frequency band, see FIG. 4 at (b). The energies in the frequency bands were normalized to the total energy of the signal, which was calculated by the area under the entire FFT spectrum, see FIG. 4 at (b). These normalized energies for different frequency bands are referred to as frequency-based features in this disclosure. FIG. 4 at (b) shows the extraction of frequency-based features in the range of 80-120 kHz.

Figure 5:
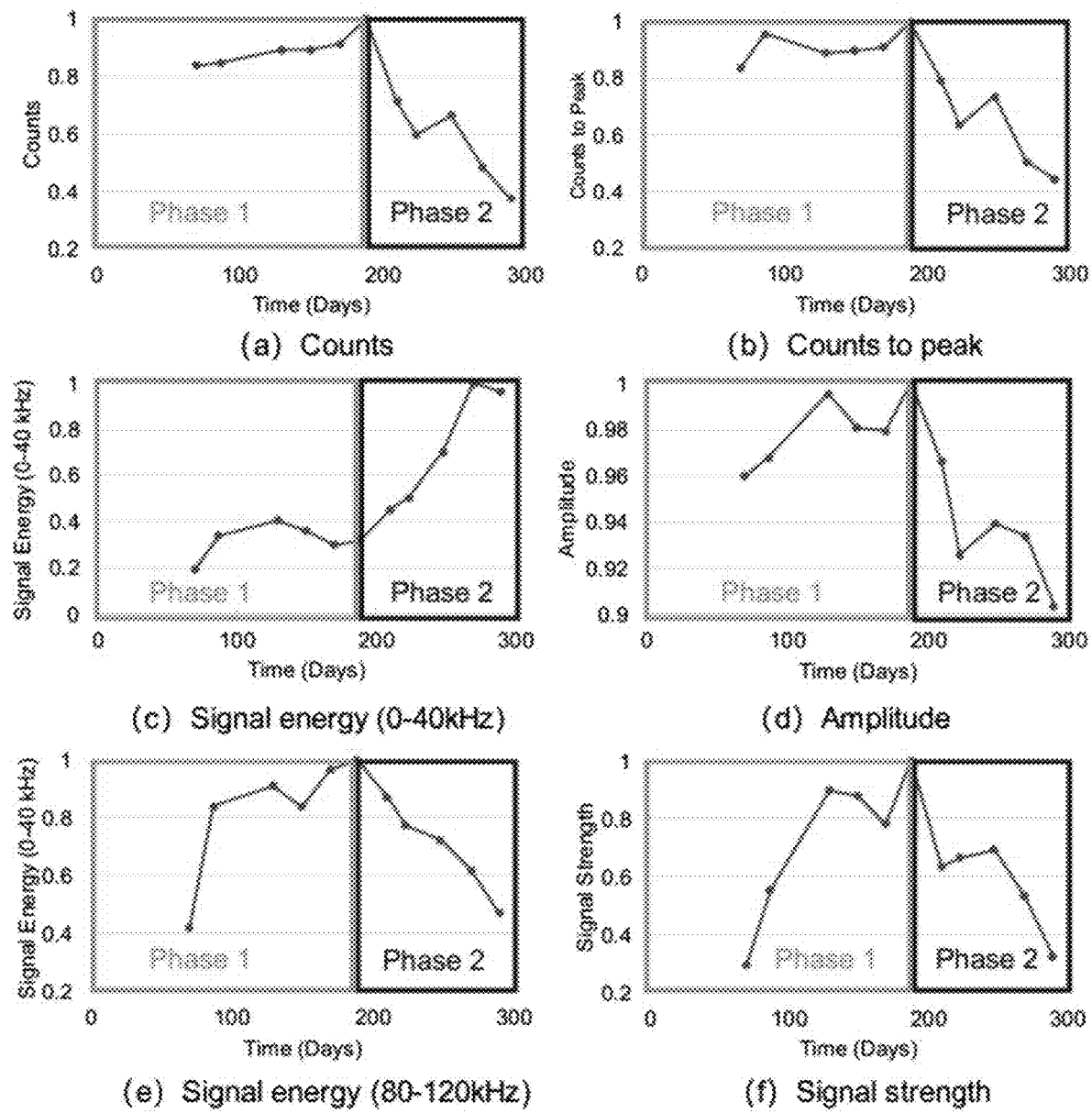
FIG. 5 shows temporal evolution of AE features during an ASR process at: (a) counts; (b) counts to peak; (c) signature energy (0-40 kHz); (d) amplitude; (e) signal energy (80-120 kHz); and (f) signal strength.

The average temporal evolution of some features such as counts, counts to peak, amplitude, signal strength, signal energy for 0-40 kHz, and signal energy for 80-120 kHz are illustrated in FIG. 5. All the features were normalized to their maximum value. The features shown in FIG. 5 indicates the change in the temporal evolution at almost the same time: around 190 to 200 days. The ASR process can be divided into two phases (phase 1 and phase 2) according to the observed trend.

Figure 6:
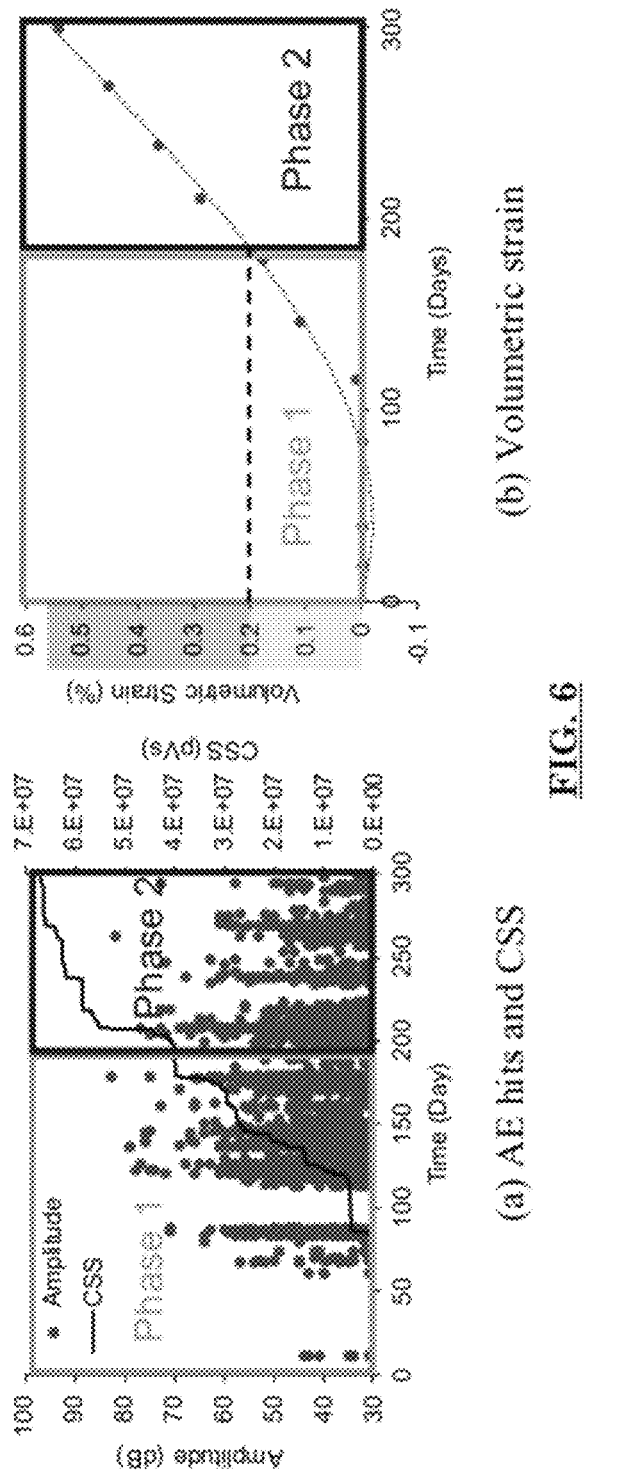
FIG. 6 shows AE amplitudes and volumetric strain presentations with designated classes at: (a) AE hits and CSS and (b) volumetric strain.

The signal amplitudes and the cumulative signal strength (CSS) for the concrete specimen are presented in FIG. 6 at (a). The jumps in the cumulative signal strength curve are representative of a new crack initiation event or a crack extension along an existing crack. The major jump occurs around 200 days, which coincides with the time related to change in AE features shown in FIG. 6. Therefore, day 190 was employed to divide the ASR process into the first and second phases. The phase definition is deployed as the label of AE signals in the deep learning models.

The strain measurements were conducted along different dimensions on the specimen surfaces during ASR. The volumetric strain is defined as the accumulation of average strains along the X, Y, and Z axes. Results of the volumetric strain range is presented in FIG. 6 at (b). In phase 1, the strain range changes from 0% to 20%, and in phase 2, the strain range changes from 20% to 55%.

Waveforms and CWT Images

Figure 7:
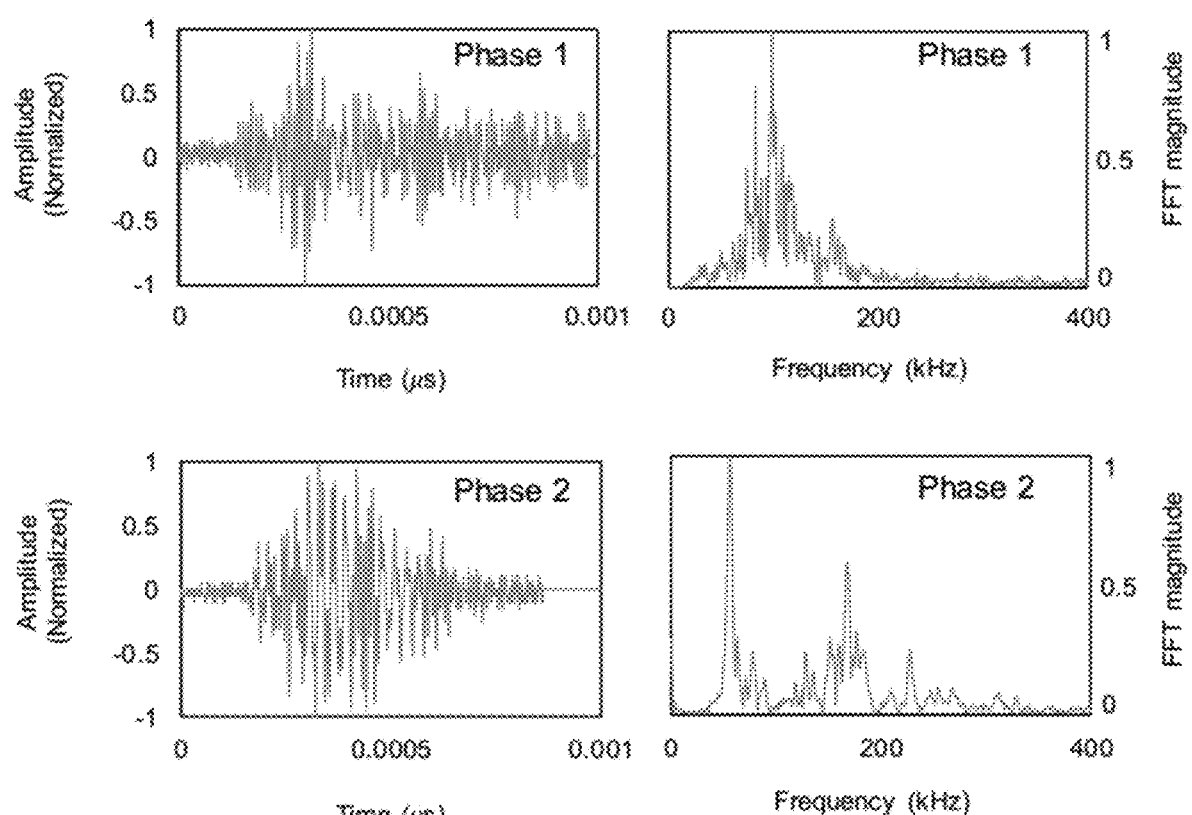
FIG. 7 shows waveforms of AE signals in phase 1 and 2.
Figure 8:
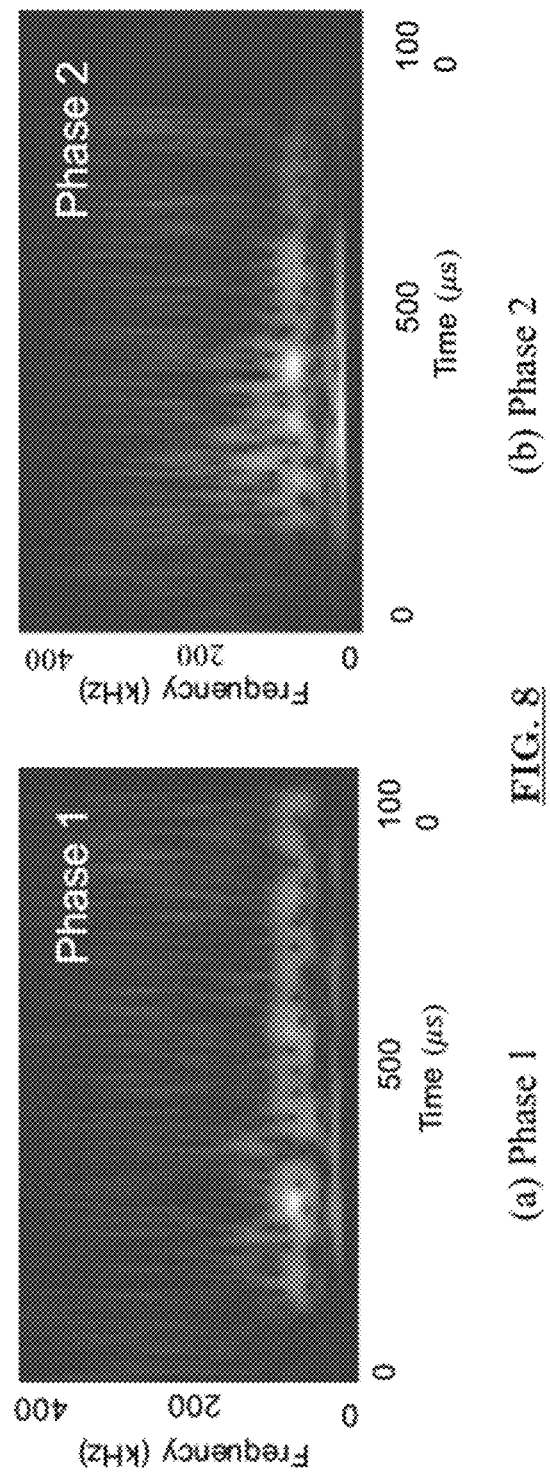
FIG. 8 shows CWT image of AE signals in class 1 and 2 at: (a) phase 1; and (b) phase 2.

There are 1668 and 1402 AE signals in class 1 and 2, respectively. The input set for the stacked autoencoder was an FFT spectra of AE signals. The other data set was prepared by conducting CWT on the data. The coefficients of CWTs were saved as 2D contour images, and the images were utilized as an input data set for CNN. Both deep learning models (autoencoder and CNNs) classify the AE signals into the attributed classes. A time-domain waveform and its FFT spectrum are randomly selected for each class and presented in FIG. 7. Moreover, the CWT images of the signals are presented in FIG. 8. The amplitudes of AE waveforms were normalized to a range of −1 to 1. The frequency-domain waveforms were normalized by the maximum magnitudes, and the wavelet coefficients were scaled between 0 to 1.

Evaluation of ASR Data Using CNN

Classification Using all AE Signals

Figure 9:
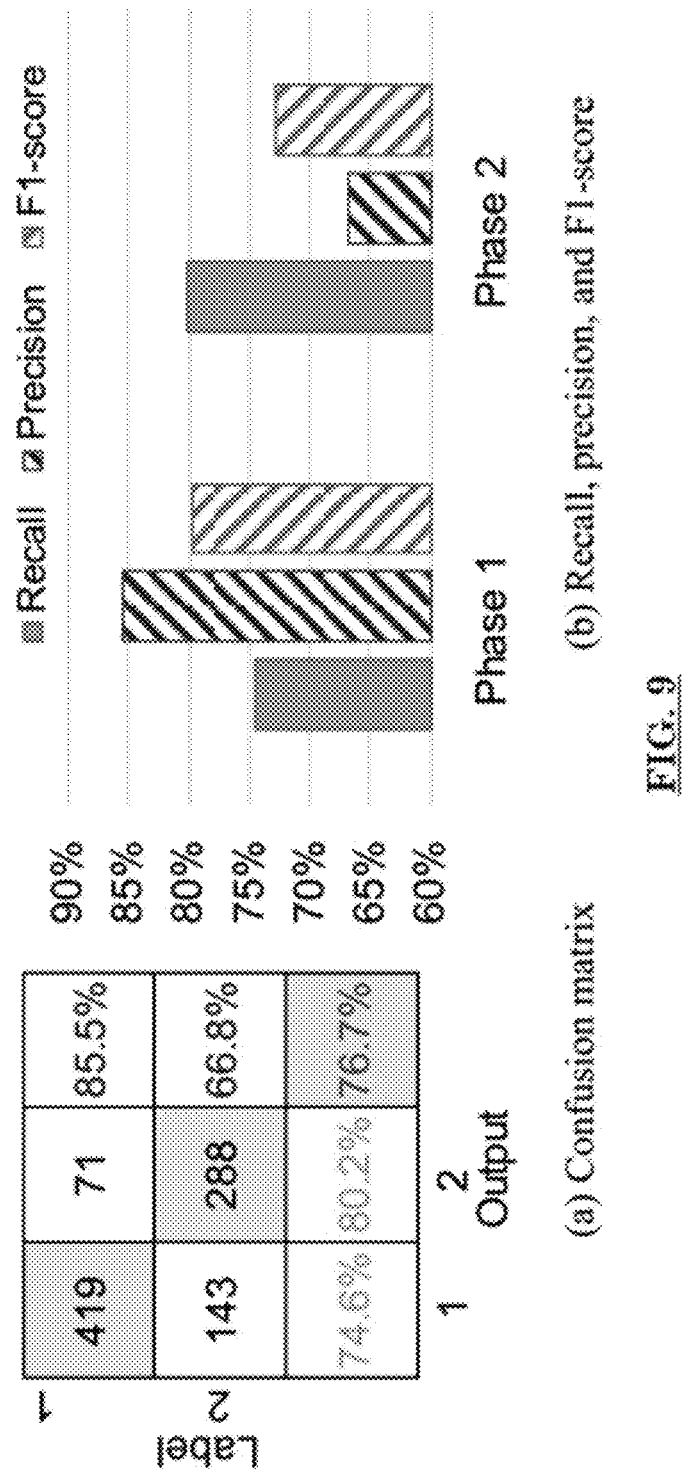
FIG. 9 shows performance of CNN using all AE signals at: (a) confusion matrix; and (b) recall, precision and F1-score.

From all CWT contour images, 70% of images were randomly selected for a training set of CNN and 30% of images were randomly selected for a validation set. The designated phases (phase 1 or 2) were utilized as data labels. The classification result of validation dataset is presented in the confusion matrix, see FIG. 9 at (a). Among the CWT images in phase 1, 74.6% of the images were correctly classified as phase 1, while 25.4% of the images were classified as phase 2. Among the images in phase 2, 80.2% of the images were correctly classified, while 19.8% of the images were misclassified as phase 1. In total, 707 images were correctly classified to the corresponding phases, which constituted 76.7% of all images in the validation data set. In other words, the accuracy of the CNN classifier is 76.7%, see FIG. 9 at (a). Precision and recall are employed as parameters to evaluate the classification performance in each phase. Generally, precision can be calculated by Eq. (1):

$$\text{Precision} = \frac{TP}{TP + FP} \quad (1)$$

Where, TP is the true positive, and refers to the number of samples which are correctly classified to the attributed class. FP is the false positive, which refers to the number of samples that do not belong to the class but are misclassified into the class. The precisions of the CNN model using all AE data for class 1 and 2 are 85.5% and 66.8%, respectively, see FIG. 9 at (a).

The recall parameter can be calculated as follows:

$$\text{Recall} = \frac{TP}{TP + FN} \quad (2)$$

Where FN is the false negative, which is the number of samples that belong to a class but are misclassified as other classes. The recall parameter of class 1 and 2 for the CNN model was calculated as 74.6% and 80.2%, see FIG. 9 at (a).

The precision parameter has an inverse relationship with the recall parameter. Generally, a class with high precision value has a low recall value and vice versa (see, Buckland, M., Gey, F. 1994. *The relationship between recall and precision. Journal of the American society for information science*, 45(1), 12-19.). The F1-score is a parameter to evaluate the efficiency of the classifier in each phase (class) by considering both recall and precision parameters.

The F1-score is the harmonic mean of the precision and recall (see, Zhong, L., Hu, L., Zhou, H. 2019. *Deep learning based multi-temporal crop classification. Remote sensing of environment*, 221, 430-443.). The values of the F1-score for phase 1 and phase 2 are 79.7% and 72.9%, respectively and are presented in FIG. 9 at (b).

Classification Using AE Signals Recorded by a Single Sensor

Figure 10:
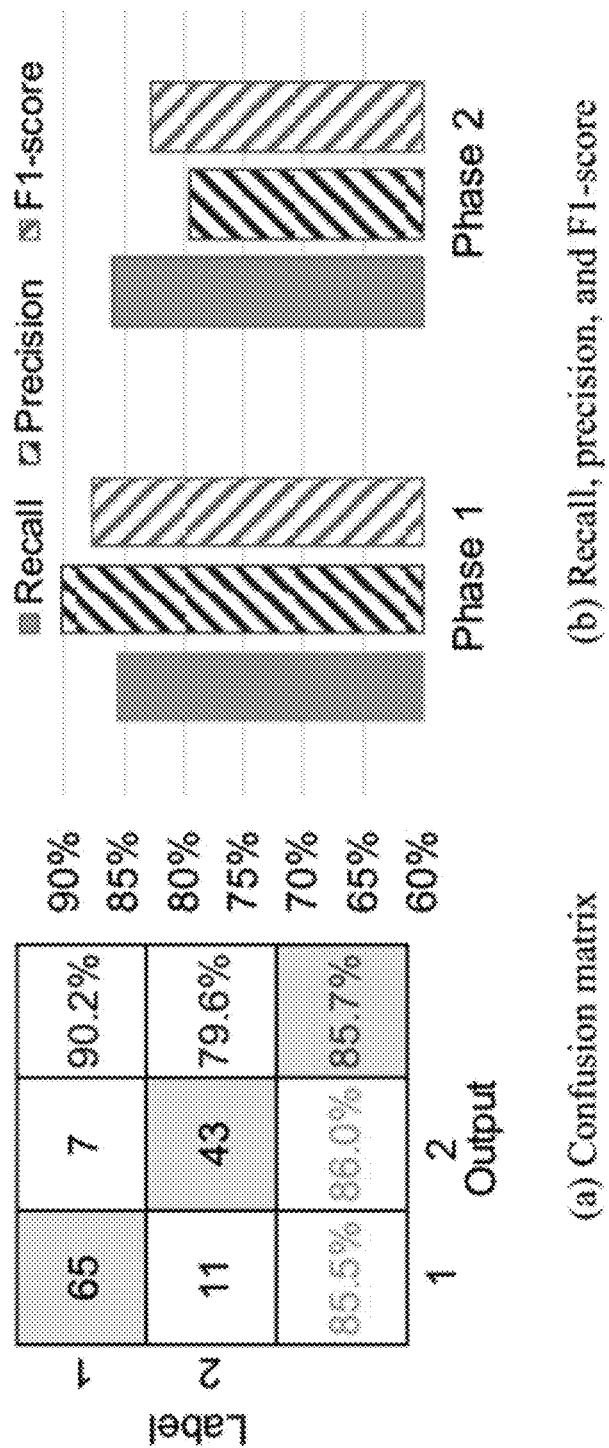
FIG. 10 shows performance of CNN model using data from a single sensor at: (a) confusion matrix; and (b) recall, precision and F1-score.

A CNN model was developed using the data from one sensor. The selected sensor had the largest number of AE signals (421) of all the sensors. AE signals were transferred to CWT images. From all images, 70% of the data were randomly selected for the training set and the rest (30%) were employed for the validation set. The result of the CNN model is presented in FIG. 10 at (a). Of the images in phase 1, 85.5% were correctly classified as phase 1, and 14.5% of the images were misclassified as phase 2. Among the images in phase 2, 86.0% were successfully classified with 14.0% of the images being erroneously assigned to phase 1. The total accuracy of the model is 85.7%, FIG. 10 at (a). The precisions of phase 1 and 2 are 90.2% and 79.6%, respectively, see FIG. 10 at (a). The recall parameters for phase 1 and 2 are 85.5% and 86.0%, respectively (FIG. 10 at (a).). The F1-score values for phases 1 and 2 are 87.8% and 82.7%, respectively (FIG. 10 at (b)).

Evaluation of ASR Using Stacked Autoencoder

Figure 11:
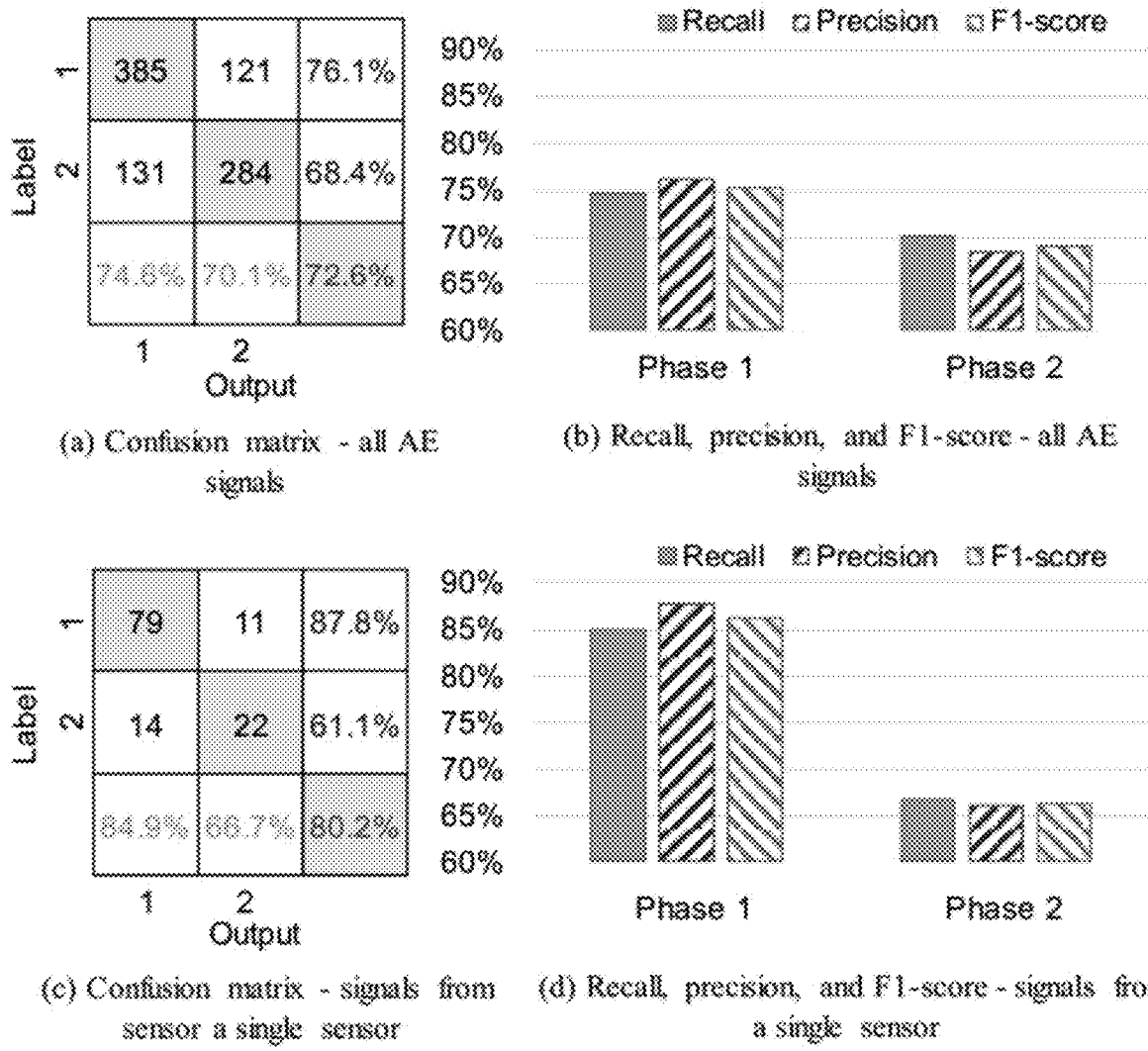
FIG. 11 shows performance of stacked autoencoder at: (a) confusion matrix—all AE signals; (b) recall, precision, and F1-score—all AE signals; (c) confusion matrix—signals from a single sensor; and (d) recall, precision, F1-score—signals from a single sensor.

The FFT magnitudes of AE signals were employed as the input for the stacked autoencoder models. The ratios of training and validation data for the autoencoder models were consistent with the selected ratios for CNN models. The assigned classes (phases) for the AE signals were utilized as the data labels, similar to the CNN models. The results are presented in FIG. 11. The accuracy of classification using all signals is 72.6%. The precision parameters for phase 1 and 2 are 76.1% and 68.4%, respectively. The recall parameter for phase 1 and 2 are 74.6% and 70.1%, respectively (FIG. 11 at (a)) and the F1-score parameter for phase 1 and 2 are 75.4% and 69.2%, respectively (FIG. 11 at (b)). Using signals from a single sensor, the total accuracy of classification for the autoencoder model is 80.2%. The precision values for phase 1 and 2 are 87.8% and 61.1%, respectively. The recall values of phase 1 and 2 are 84.9% and 66.7%, respectively (FIG. 11 at (c)). The F1-score values for phase 1 and 2 are 86.3% and 66.4%, respectively (FIG. 11 at (d)).

Comparison and Discussion

The classification accuracies of CNN and stacked autoencoders are presented in Table 1, see FIG. 13. As seen in Table 1, the models using data from a single sensor indicates a higher accuracy than the models using all data. Furthermore, the CNN models have higher classification accuracies than the autoencoder models. The accuracy of the CNN model using the data from a single sensor is the highest among the evaluated methods (85.2%).

Figure 12:
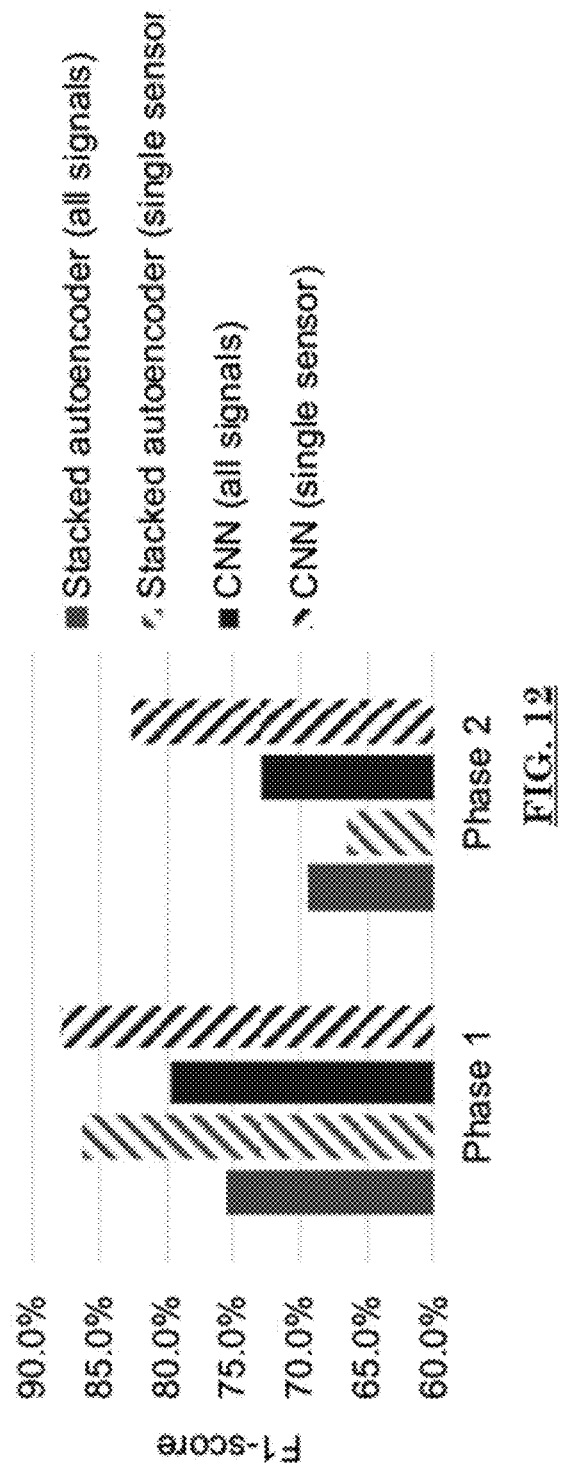
FIG. 12 shows F1-score of phase 1 and phase 2.

The F1-score parameters for all models are presented in FIG. 12. F1-score values of the CNN model using data from the single sensor are generally the highest and are relatively consistent between the classes (FIG. 12). However, a notable difference of F1-scores in two classes can be observed in the autoencoder models (FIG. 12).

The CNN model using data from the single sensor has the highest accuracy and the most consistent performance between the two classes. Therefore, the CNN model is a better option to estimate the range of ASR volumetric strains from AE signals than the autoencoder models.

The evaluation method based on deep learning is proposed to assess the condition of ASR progress in concrete structures. To verify the effectiveness of the proposed method, a concrete specimen with reactive coarse aggregates and reinforcements was cast and placed in a chamber for 300 days to accelerate the ASR by providing high temperature and humidity. AE sensors were affixed on the specimen surfaces to acquire stress waves emitted during the ASR due to cracking. The ASR expansion was measured using DEMEC gauge on a regular basis. A CNN and stacked autoencoder models were trained using the AE data for the classification purposes and determining ASR volumetric strain ranges. The main conclusions of the disclosure are summarized as follows:

Both the CNN and stacked autoencoder can classify the AE signals to their ASR phases with an acceptable accuracy. However, a higher accuracy was observed in the classification using the CNN than the stacked autoencoder. In addition, using AE signals from a single sensor lead to a better performance of classification than using signals captured by all the sensors.

The F1-scores indicated that the classification result of CNN using signals from a single sensor has the best performance in both phases (classes). Moreover, a good consistency of F1-scores between two phases was observed for the CNN models.

Considering both global accuracy and classifier performance in two phases, the CNN model using the data from a single sensor is the most efficient model among the evaluated models to monitor the temporal evolution of the concrete specimen affected by ASR.

Some conventional approaches have been used for the inspection and monitoring of ASR progress and damage evaluation in concrete structures. Those approaches include visual inspection, coring, and petrographic analysis. Those approaches have been widely utilized for decades, but they have some drawbacks. For instance, a visual inspection cannot be employed to detect early ASR damage because ASR damage usually initiates inside concrete structures and appears on the surface in later stages of the ASR process. Petrographic analysis can detect the early ASR damage inside concrete structures; however, this approach is intrusive, restricting its application in sensitive structures such as nuclear power plants. In addition, it is time-consuming and subject to human error. To improve the reliability and efficiency of ASR monitoring, an automatic non-destructive monitoring approach of ASR damage is thereby needed.

Acoustic emission (AE) is a non-destructive structural health monitoring method that could be an option for monitoring ASR. AE is also referred to as a physical phenomenon when stress waves are generated by the rapid release of elastic energy during cracks or damage formation. AE signals can be detected and collected by AE sensors attached to structures. The method of recording and processing AE signals to diagnose the health status of structures is AE monitoring. AE is a sensitive method and has a continuous monitoring capability and has been utilized for the evaluation of ASR damage in concrete structures. Abdelrahman et al., see M. Abdelrahman, M. K. ElBatanouny, P. Ziehl, J. Fasl, C. J. Larosche, J. Fraczek, 2015. *Classification of alkali-silica reaction damage using acoustic emission: A proof-of-concept study, Construction and Building Materi-* als 95 406-413, investigated the AE monitoring of ASR damage in three small-scale concrete specimens. The results indicated that the rate of AE activity is correlated to the rate of ASR damage, and AE intensity analysis can be used to classify ASR damage. Soltangharaei et al., see V. Soltangharaei, R. Anay, L. Ai, E. R. Giannini, J. Zhu, P. Ziehl, 2020. *Temporal Evaluation of ASR Cracking in Concrete Specimens Using Acoustic Emission, Journal of Materials in Civil Engineering* 32 04020285, evaluated the ASR progress in concrete structures with different internal restraints by using AE. Unsupervised pattern recognition is employed to analyze AE signals. Previous research has proven that AE is a reliable technique for monitoring and evaluating ASR progress in concrete structures. However, traditional analyzing methods of AE signals are usually based on experience and very challenging, especially for complex data sets. Therefore, an intelligent algorithm is needed to assist in analyzing AE data in real-time and alert ASR damage stages.

Machine learning is an intelligent data processing technique. By learning the feature extracted from the data, machine learning can understand the pattern of data and make a decision. See, I. Goodfellow, Y. Bengio, A. Courville, 2016. *Machine learning basics, Deep learning* 1 98-164. Machine learning models such as artificial neural network, support vector machine (SVM), K-nearest neighbor (KNN), AdaBoost and random forest (RF) has been widely utilized for signal processing. See, V. Cherkassky, Y. Ma, 2004. *Practical selection of SVM parameters and noise estimation for SVM regression, Neural networks* 17 113-126; I. W. Tsang, J. T. Kwok, P.-M. Cheung, N. Cristianini, 2005. *Core vector machines: Fast SVM training on very large data sets, Journal of Machine Learning Research* 6; H. Zhang, A. C. Berg, M. Maire, J. Malik, 2006, *SVM-KNN: Discriminative nearest neighbor classification for visual category recognition, IEEE,* 2126-2136; M. Belgiu, L. Drăguţ, 2016. *Random forest in remote sensing: A review of applications and future directions, ISPRS journal of photogrammetry and remote sensing* 114 24-31; R. Sun, Y. Chen, A. Dubey, P. Pugliese, 2021. *Hybrid electric buses fuel consumption prediction based on real-world driving data, Transportation Research Part D: Transport and Environment* 91 102637; L. Ai, V. Soltangharaei, R. Anay, M. J. van Tooren, P. Ziehl, 2020, *Data-Driven Source Localization of Impact on Aircraft Control Surfaces, IEEE,* 1-10; L. Ai, V. Soltangharaei, M. Bayat, B. Greer, P. Ziehl, 2021. *Source localization on large-scale canisters for used nuclear fuel storage using optimal number of acoustic emission sensors, Nuclear Engineering and Design* 375 111097; and L. Ai, V. Soltangharaei, W. d. Backer, P. Zieh, M. v. Tooren, 2020. *A Minimally Intrusive Impact Detection System for Aircraft Moveable using Random Forest, CAMX* 2020.

One of the limitations of machine learning methods is nonautomatic feature extraction. In these methods, feature selection depends on human experience, and some important features may be overlooked. This limitation can be overcome by using architecture selection methods to indicate the feature importance based on statistical sensitivity analysis, see F. Albu, A. Mateescu, N. Dumitriu, 1997, *Architecture selection for a multilayer feedforward network,* 131-134; B. Dorizzi, J. Mota, F. Albu, 1997, *A step towards equalization for radiomobile channel: Neural Networks and Variable Selection*. Albu et al. proposed an architecture selection method for a multilayer feedforward network. The method can indicate the importance of input features by analyzing the partial derivatives of output with regard to the input features. Utilizing deep learning methods can be another way to overcome the limitation. Deep learning methods are improved intelligent techniques which are based on machine learning. It can automatically learn features from complex data sets without feature extractions. See, I. Goodfellow, Y. Bengio, A. Courville, Y. Bengio, 2016, *Deep learning, MIT press Cambridge*. CNN is one of the relatively new deep learning algorithms, which is widely studied in image recognition, see A. Krizhevsky, I. Sutskever, G. E. Hinton, 2012, *Imagenet classification with deep convolutional neural networks,* 1097-1105; and L. Ai, V. Soltangharaei, P. Ziehl, 2021. *Evaluation of ASR in concrete using acoustic emission and deep learning, Nuclear Engineering and Design* 380 111328, object detection, see F. Guo, Y. Qian, Y. Shi, 2021. *Real-time railroad track components inspection based on the improved YOLOv4 framework, Automation in Construction* 125 103596, and semantic segmentation, see F. Guo, Y. Qian, Y. Wu, Z. Leng, H. Yu, 2021. *Automatic railroad track components inspection using real-time instance segmentation, Computer-Aided Civil and Infrastructure Engineering* 36 362-377. Combining various machine learning and deep learning models is a strategy to improve model performance. See, Panigrahy et al. D. Panigrahy, P. Sahu, F. Albu, 2021. *Detection of ventricular fibrillation rhythm by using boosted support vector machine with an optimal variable combination, Computers & Electrical Engineering* 91 107035 combined SVM and AdaBoost to improve the detection of ventricular fibrillation (VF) rhythm. Taherkhani et al. A. Taherkhani, G. Cosma, T. M. McGinnity, 2020, *AdaBoost-CNN: An adaptive boosting algorithm for convolutional neural networks to classify multi-class imbalanced datasets using transfer learning,* 351-366, integrated AdaBoost model with a CNN model to deal with large imbalanced datasets with high accuracy.

In recent years, machine learning and deep learning have been applied to AE data in many applications, such as metallic structures, see A. Ebrahimkhanlou, B. Dubuc, S. Salamone, 2019. *A generalizable deep learning framework for localizing and characterizing acoustic emission sources in riveted metallic panels, Mechanical Systems and Signal Processing* 130 248-272., aircraft components L. Ai, V. Soltangharaei, M. Bayat, M. van Tooren, P. Ziehl, 2021. *Detection of impact on aircraft composite structure using machine learning techniques, Measurement Science and Technology,* and rail track monitoring, see D. Li, Y. Wang, W.-J. Yan, W.-X. Ren, 2020. *Acoustic emission wave classification for rail crack monitoring based on synchrosqueezed wavelet transform and multi-branch convolutional neural network, Structural Health Monitoring* 1475921720922797. Ebrahimkhanlou et al. proposed a deep learning framework based on a stacked autoencoder network to locate AE events on the metal structures. Ai et al. developed a passive non-destructive health monitoring system to locate impacts on an aircraft component based on AE, random forest, and stacked autoencoder network. Li et al. utilized a multi-branch CNN model for AE wave classification to obtain a more accurate and comprehensive monitoring system.

Machine learning, deep learning, and AE have also been employed to evaluate the time-dependent damage stages of composite materials and metallic materials, see A. Nasiri, J. Bao, D. Mccleeary, S.-Y. M. Louis, X. Huang, J. Hu, 2019. *Online Damage Monitoring of SiC f-SiC m Composite Materials Using Acoustic Emission and Deep Learning, IEEE Access* 7 140534-140541; and S.-X. Chen, L. Zhou, Y.-Q. Ni, X.-Z. Liu, 2020. *An acoustic-homologous transfer learning approach for acoustic emission-based rail condition evaluation, Structural Health Monitoring* 1475921720976941. Nasiri et al. investigated on online monitoring of degradation process in a composite specimen. Three different stages of degradation: elastic, matrix-driven, and fiber-driven behavior, have been defined. The researchers identify different degradation stages of the specimen by classifying the AE events into one of the three different classes. Chen et al. employed AE for the monitoring of railways. An AE sensor was attached on the rail and the entire monitoring process was divided into four stages according to the mechanism of fatigue growth. An acoustic-homologous transfer learning approach was developed to classify the AE signals into their corresponding stages.

Previous studies indicated using AE and different classification models to evaluate time-dependent damage stages in one specimen. The development process of ASR in concrete can also be divided into several phases since ASR is a time-dependent phenomenon. See, W. Wallau, S. Pirskawetz, K. Voland, B. Meng, 2018. *Continuous expansion measurement in accelerated concrete prism testing for verifying ASR-expansion models*, Materials and Structures 51 1-15. Therefore, classification models can be trained to identify the ASR damage stages based on received AE data. The authors are currently not aware of similar published studies implementing deep learning and machine learning classification algorithms to recognize the ASR damage phases using AE data. Therefore, this disclosure investigates a novel ASR monitoring and evaluation approach by employing AE, machine learning, and deep learning algorithms to fill the prementioned gap. The temporal degradation process of a concrete specimen was divided into different stages according to damage mechanisms. The AE signals emitted from different damage mechanisms had different signal signatures. Therefore, the temporal ASR damage evaluation of a specimen was mapped as a classification problem. The input was an AE signal at a given timeslot, and the output was the associated damage stage category. CNN and random forest models were utilized herein to analyze the signatures of AE signals captured during the ASR process and determine the ASR damage stage of concrete based on the AE signals. A heterogeneous ensemble learning framework was designed and proposed to combine CNN and random forest models to consider results from all combined models.

Materials and Experimental Setup
Specimen and Material

Figure 15A:
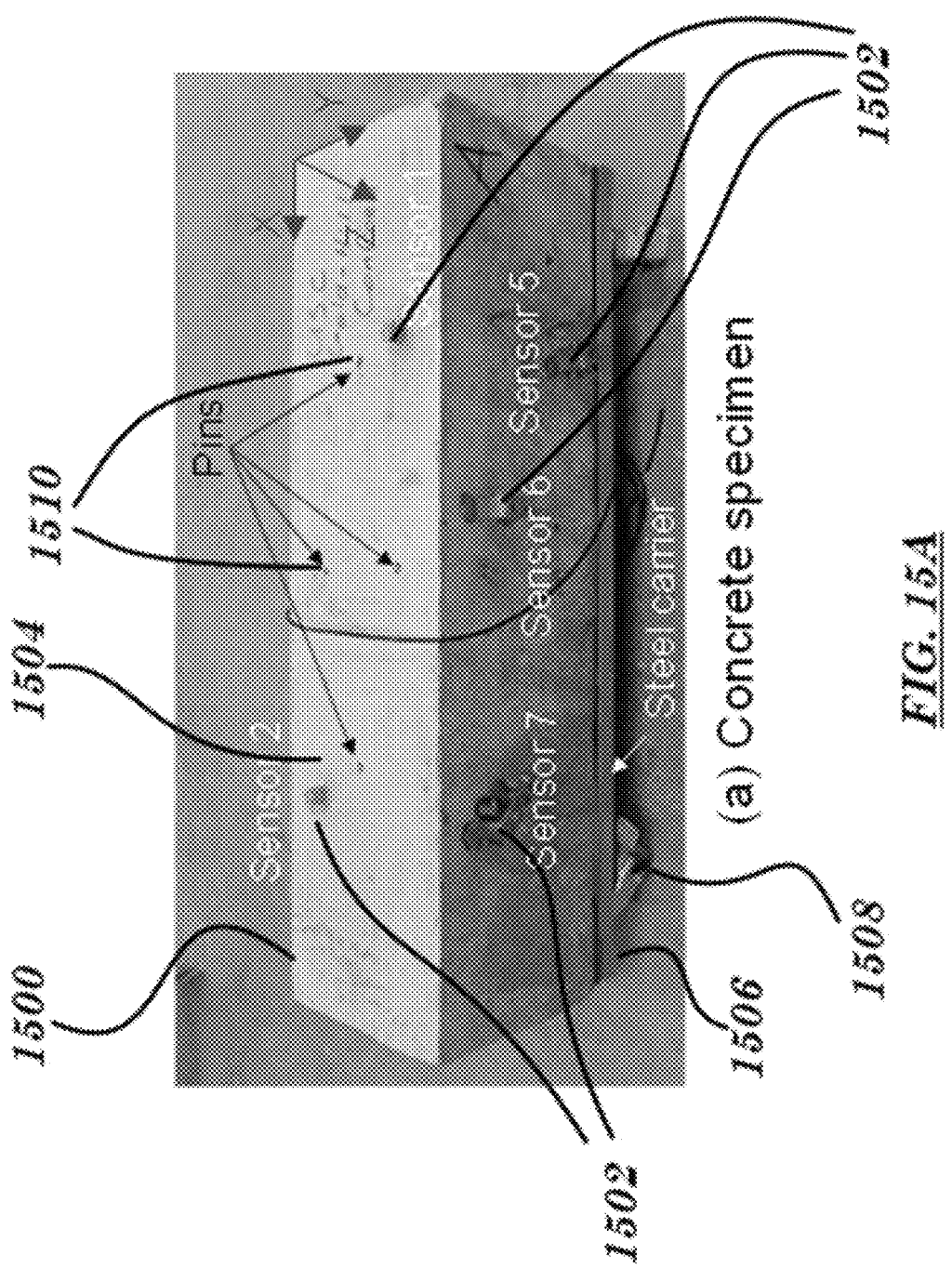
FIG. 15A shows a specimen examined pursuant to the current disclosure.
Figure 15B:
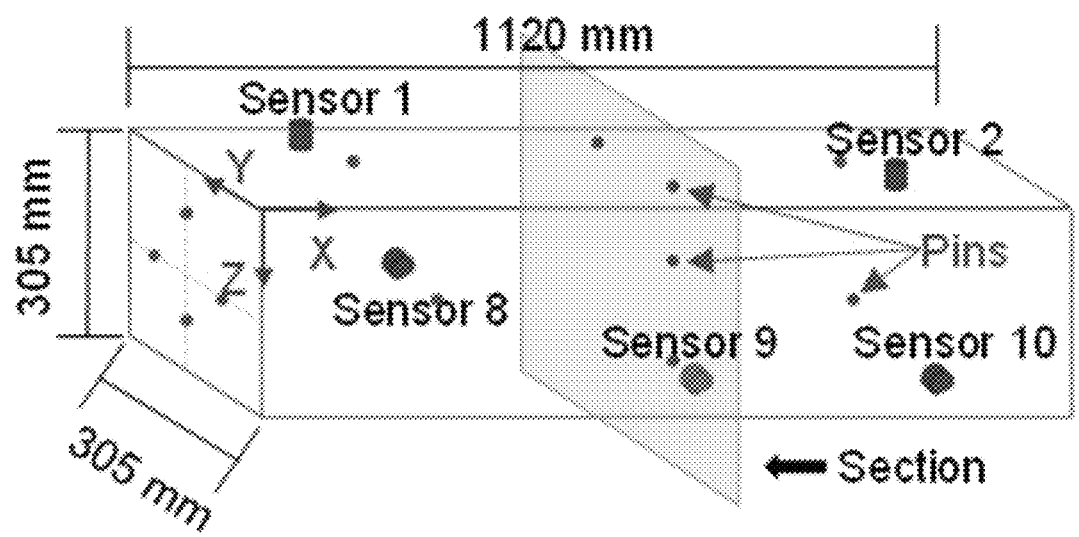
FIG. 15B shows a three-dimensional representation of sensor and pin placement on the specimen of FIG. 15A.
Figure 15C:
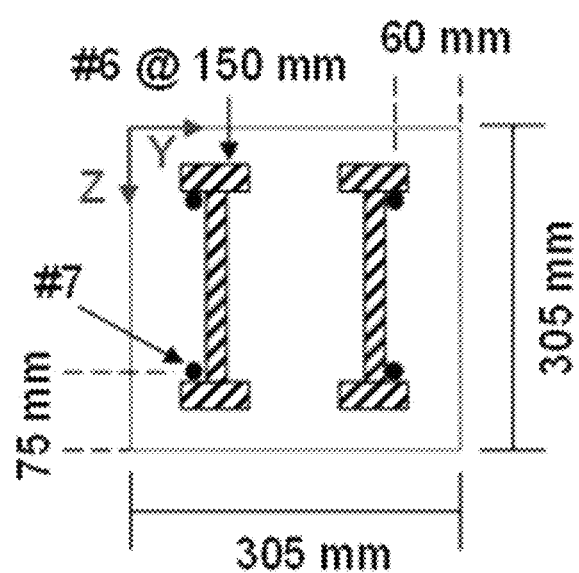
FIG. 15C shows reinforcement details of the specimen of FIG. 15A.

In this disclosure, a concrete block specimen 1500 reinforced by steel rebars, not shown, was prepared. The geometrics of the concrete specimen 1500 is presented in FIG. 15B. The dimensions of the block are 305 mm×305 mm×1120 mm. The rebar details are shown in FIG. 15C. The specimen had four longitudinal US #7 steel rebars and US #6 steel rebars with 150 mm spacing as transverse reinforcement. All rebars were T-headed to compensate for the short development length.

The concrete specimen 1500 has a 0.5 cement to water ratio. The cement used in the mixture was an ASTM C150, see ASTM, ASTM C150/C150M-20 Standard Specification for Portland Cement, Retrieved May 9, 2021, from www.astm.org/Standards/C150, Type I/II low-alkali cement with 0.48% $Na_2Oeq$. Crushed greenschist from North Carolina was utilized as a reactive coarse aggregate. Sodium hydroxide (NaOH) was added to the concrete mixture to accelerate the development of ASR. Details of the materials can be found in Table 2.

Acoustic Emission Instrument Setup

Ten AE sensors 1502 were utilized to collect AE events captured during the ASR experiment. The AE sensors were attached to the concrete specimen by using grey double/bubble epoxy. FIG. 15 at a shows the attached sensors 1502 on the concrete specimen 1500 (cables were not connected) before conducting the test. The dimension of the specimen and layout of the sensors can be found in FIG. 15B. Sensors 1-2 were attached to the top surface. Sensors 3-4 were attached to the bottom. Sensors 5-7 were attached on the backside surface, and Sensors 8-10 were attached on the front side surface. All AE sensors 1502 in this disclosure were wideband type PKWDI with 26-dB internal preamplification. The sensors have an operating frequency range of 200-850 kHz. An attenuation test has been conducted to verify the sensitivity of PKDWI sensors by performing the Hsu-Nielsen pencil lead break, see N. N. Hsu, 1977, *Acoustic emissions simulator, Google Patents*. The results indicated that sensors 1502 were sensitive to receive the signals from the farthest location on the specimen surface 1504. The hardware and software of the AE system were produced by MISTRAS Group, Inc. (Princeton Junction, NJ, USA). AE signals were acquired by a 24-channel Micro-II Express acquisition system. The pre-trigger time, hit definition time (HDT), peak definition time (PDT), and hit lockout time (HLT) were set to 256 μs, 400 μs, 200 μs, and 200 μs, respectively. The sampling rate was set to 5000 kHz. The signal length was set as 1024 μs. Therefore, each signal has 5120 data points. Before the experiment, the level of background noise in the chamber room was tested. Most of the background noise were below 32 dB (ref 1V/(m/s)). Therefore, the threshold in the experiment was set to 32 dB (ref 1V/(m/s)) during the monitoring. The AE signals with the amplitude higher than the threshold were recorded. The low and high pass digital filters were set to 20 kHz, and 400 kHz, respectively.

Experiment Procedures

During the experiment, the concrete specimen 1500 was sealed in a chamber, not shown, with dimensions of 243 cm×243 cm×122 cm. A steel carrier 1506 with wheels 1508 (as seen in FIG. 15A) was designed and built to be employed as a support for the concrete specimen. The ASR process accelerated, providing high humidity (95%+5%) and a high temperature (37+3° C.) in the chamber. Neoprene pads were employed between the specimen bottom surface and steel carrier to minimize the effect of vibrations from the ground. Pins 1510 (as seen in FIGS. 15A and 15B) were affixed on surface 1504 of concrete specimen 1500 using grey double/bubble epoxy for expansion strain measurements. The distance between pins 1510, along the X-axis, was 500 mm. The distances between pins 1510 along the Y and Z axes were 150 mm. The pin arrangement on the right and back surfaces of the specimen 1500 were identical to those on the left and front surfaces. The specimens were monitored for 460 days in the chamber, and AE was recorded in time. The ASR expansions were measured monthly using DEMEC gauges (demountable mechanical strain gauges) on the pin locations. The monthly maintenance of AE sensors was conducted to ensure the strong bonding condition between sensors 1502 and specimen 1500. The first DEMEC gauge measurement was conducted on the 18th day of the experiment. Crack width measurement started on the 146th day (after observing the surface visible cracks) using a Dino-Lite digital microscope with a maximum magnification of 184× and an ELE crack detection microscope with a magnification of 40×. More detailed information on the experimental setup and procedures can be found in see Soltangharaei et al.

Methodology

The ASR evaluation method proposed in this disclosure is based on AE monitoring and a heterogeneous ensemble learning framework. The original AE waveforms acquired by the acquisition system were saved as time series. An image-based dataset was created by converting the AE waveforms to the continuous wavelet transform (CWT) images. A feature-based dataset was obtained by extracting parametric features from the AE waveforms. The detailed descriptions of the two datasets could be found infra.

Figure 17:
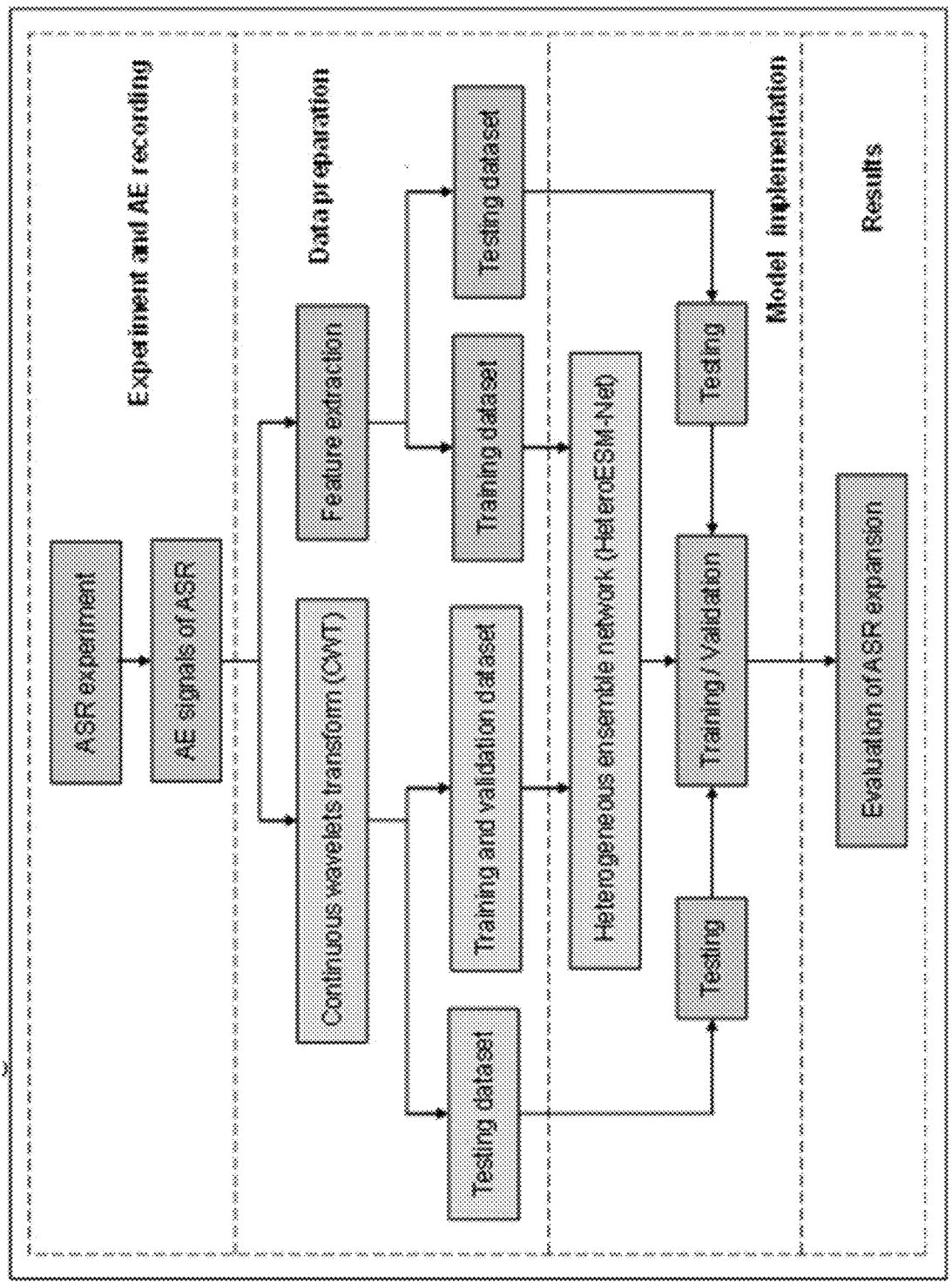
FIG. 17 shows workflow of ASR evaluation using ensemble learning framework.

Heterogeneous ensemble learning refers to the ensemble structure composed of different types of models, see J. N. van Rijn, G. Holmes, B. Pfahringer, J. Vanschoren, 2018. *The online performance estimation framework: heterogeneous ensemble learning for data streams, Machine Learning* 107 149-176. In this disclosure, a heterogeneous ensemble learning network includes convolutional neural networks (CNN) and random forest (RF) models and is employed to receive two different AE datasets. The network classifies the AE data into different ASR phases (introduced infra). The image-based dataset was divided into training, validation, and testing datasets. The feature-based dataset was divided into training and testing datasets. No validation dataset was prepared for the feature-based data. The reason will be explained infra. Prepared training/validation data was used to train the heterogeneous ensemble learning network. The testing set was used to evaluate the performance of the trained network. The ratio of the testing dataset over the whole dataset was kept the same in both the image dataset and the feature-based dataset. The procedure of the ASR expansion evaluation is presented in FIG. 17.

Continuous Wavelet Transform

CWT is a widely used joint time-frequency analysis approach highlighting time-frequency characteristics from a non-stationary signal such as AE signals, see A. Ebrahimkhanlou, S. Salamone, 2017. *Acoustic emission source localization in thin metallic plates: A single-sensor approach based on multimodal edge reflections, Ultrasonics* 78 134-145. Assume there is a signal: x(t). The CWT of the signal can be expressed as Eq. (1):

$$CWT_{(a,b)} = \frac{1}{\sqrt{|a|}} \int_{-\infty}^{\infty} x(t)\psi^*\left(\frac{t-b}{a}\right)dt \quad (1)$$

where CWT is the continuous wavelet coefficients derived from the signals, a refers to the scale index parameter which controls the scaling of wavelet function and has an inverse relation to frequency, b refers to the translation parameter which controls time-shifting of wavelets. The wavelet coefficients are derived by moving wavelets with different a scale indices through the signals. $\psi^*$ refers to the complex conjugate of mother wavelet function $\psi$. In this disclosure, Morse wavelet, see J. M. Lilly, S. C. Olhede, 2012. *Generalized Morse wavelets as a superfamily of analytic wavelets, IEEE Transactions on Signal Processing* 60 6036-6041, is selected as the mother wavelet function to conduct CWT. The Fourier transform of Morse wavelet is presented in Eq (2):

$$\Psi_{p,\gamma}(x) = U(x)\alpha_{p,\gamma} x^{\frac{p^2}{\gamma}} e^{-x^{\gamma}} \quad (2)$$

where U(x) refers to the unit step, $\alpha_{p,\gamma}$ refers to the normalizing constant, $p^2$ refers to the time-bandwidth product. $\gamma$ is the parameter that characterizes the symmetry of the Morse wavelet, see J. M. Lilly, S. C. Olhede, 2008. *Higher-order properties of analytic wavelets, IEEE Transactions on Signal Processing* 57 146-160. In this disclosure, $p^2$ was set as 60 and $\gamma$ was set as 3.

A scalogram image can be used to express the continuous wavelet coefficients. The images of AE waveforms are utilized as an input for the CNN models inside the proposed heterogeneous ensemble learning network.

Convolutional Neural Network

CNN is a class of commonly used deep neural networks that are applied for image processing, see Ai et al. CNN is composed of three main parts: the input layer, the feature extraction layers, and the fully connected (FC) layer. The input layer is used to input the test and training data. Feature extraction layers are the core of the convolutional neural network, mainly including convolutional layers and pooling layers, which cooperate to derive the features from images and learn potential patterns in the data set.

Convolutional Layer

The convolutional layers are utilized to extract the features from images. S. Albawi, T. A. Mohammed, S. Al-Zawi, 2017, *Understanding of a convolutional neural network, IEEE*, 1-6. In the convolutional layer, multiple convolutional kernels are employed to filter the input and generate feature maps, see Abawi et al. Generally, the output of the $j^{th}$ feature maps of the $n^{th}$ convolutional layer can be obtained by Eq. (3):

$$x_j^n = f\left(\sum_{i=1}^{M} x_i^{n-1} * k_{ij}^n + b_j^n\right) \quad (3)$$

where $f(\bullet)$ refers to the activation function, * refers to the operation of convolutional kernels, $k_{ij}^n$ is the kernel of the $n^{th}$ filter, $b_j^n$ is the corresponding bias matrix, $x_i^{n-1}$ refers to the input feature map transferred from the $(n-1)^{th}$ convolutional layer.

Pooling Layer

The pooling layer is used for the down-sampling of feature maps obtained from the previous convolutional layer, M. Sun, Z. Song, X. Jiang, J. Pan, Y. Pang, 2017. *Learning pooling for convolutional neural network, Neurocomputing* 224 96-104. If the image feature maps are directly utilized for the classification without any processing, a great computational complexity will be generated, and the model will be prone to overfitting. Therefore, a further reduction in the dimensionality of feature maps is required, which is the reason for the pooling layer after each convolutional layer. The input feature image is divided into mutually exclusive regions, and the feature information of adjacent image regions is aggregated for analysis. This type of down-sampling method is called pooling, see B. Graham, 2014. *Fractional max-pooling*, arXiv preprint arXiv: 1412.6071. Pooling can be divided into maximum pooling and mean pooling according to different operation modes. The general expression of the pooling layer is provided by Eq. (4):

$$x_j^n = f\left(\beta_j^n s_{down}(x_j^{n-1}) + b_j^n\right) \quad (4)$$

where $f(\bullet)$ refers to the activation function, $\beta_j^n$ and $b_j^n$ refers to the multiplicative bias and the additive bias, $S_{down}$ refers to the down-sampling function, $x_j^{n-1}$ refers to the input feature maps, $x_j^n$ refers to the output feature map after down-sampling.

Fully Connected Layer

The FC layer is employed at the end of the CNN model, see H. Nakahara, T. Fujii, S. Sato, 2017, *A fully connected layer elimination for a binarizec convolutional neural network on an FPGA*, IEEE, 1-4. It converts the feature maps that result from the previous pooling layer to one feature vector. The calculation in the $j^{th}$ FC layer can be expressed by the following equation:

$$x^j = f(x^{j-1} w^j + b^j) \quad (5)$$

where $f$ refers to the activation function, $x^{j-1}$ is the input feature maps. $x^j$ is the output value. $w^j$ and $b^j$ are the weight and bias.

Proposed Heterogeneous Ensemble Network

In this disclosure, two types of AE datasets were prepared, as mentioned before. In the CWT image-based dataset, most of the raw information of each AE waveform was retained. The CNN could learn useful time-frequency features from raw information embedded in CWT images. However, the CNN cannot learn the temporal relationship between individual signals. The AE activity has a relationship with the ASR damage, see T. Shin, V. Soltangharaei, P. Ziehl, Y. Zhang, 2019. *Prediction of Volumetric Strain in Concrete Due to ASR Reactions Using Acoustic Emission Technique and Artificial Neural Network*, Structural Health Monitoring 2019. Therefore, an AE feature-based dataset was prepared. In this dataset, a feature named "Hit rate" was calculated based on the number of acquired AE hits in terms of time. The hit rate of an AE signal was calculated by counting the number of hits that occurred in a certain number of hours before and after the current hit (Eq. (6)).

$$HR(h) = \text{Hit}_{before}(h/2) + \text{Hit}_{after}(h/2) \quad (6)$$

where HR(h) refers to the hit rate of a signal per h hours. $\text{Hit}_{before}(h/2)$ refers to the number of AE hits that were received h/2 hours before the current hit. $\text{Hit}_{after}(h/2)$ refers to the number of hits that were recorded h/2 hours after the current hit. In this disclosure, h was set to 24 hours.

Figure 18:
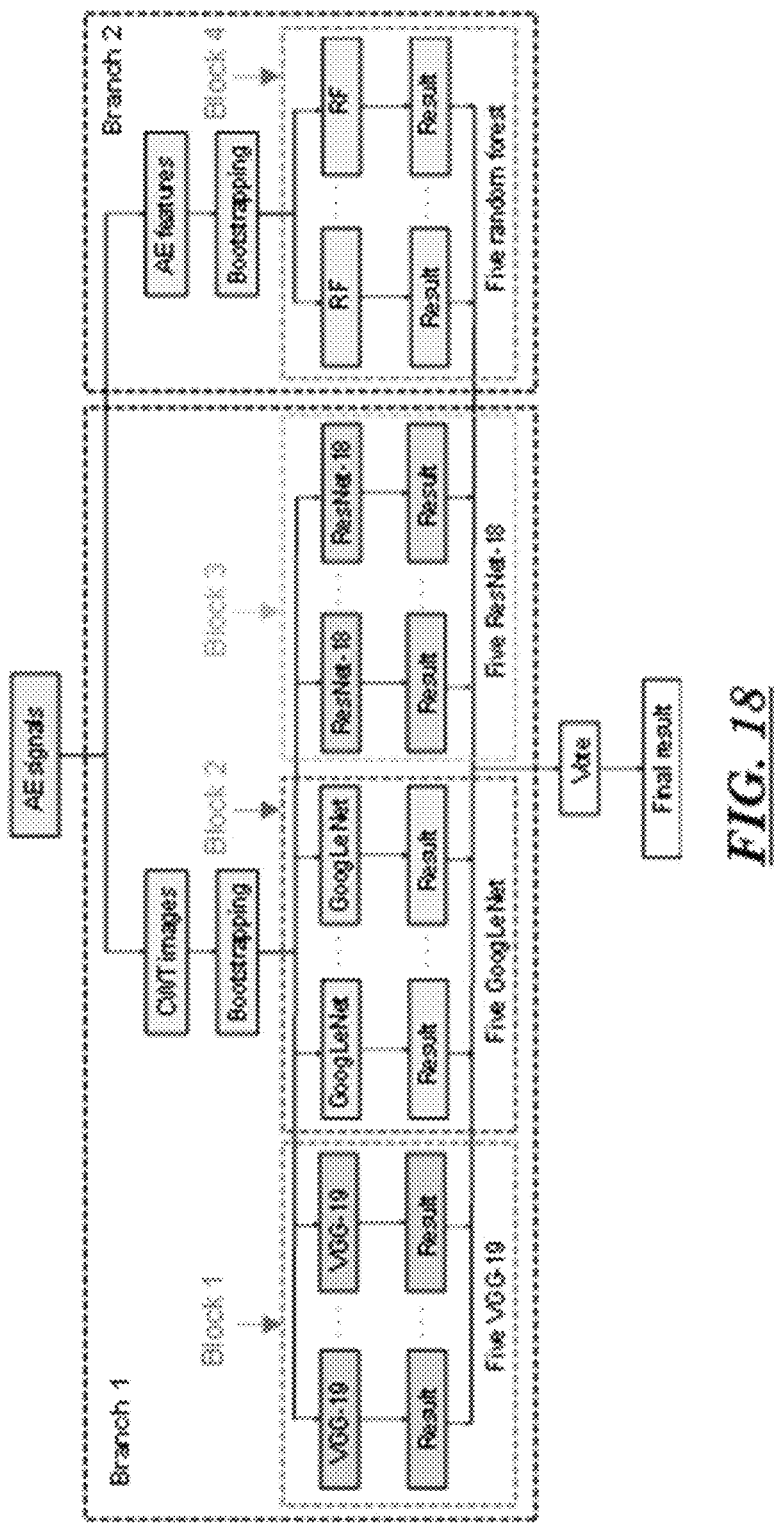
FIG. 18 shows one embodiment of a structure of the proposed RGVF-HeteroESM-Net.

AE-based features will be elaborately explained infra. A heterogeneous ensemble network including CNN models and machine learning models was proposed to include both the CWT images, and the AE features. The structure of the proposed ensemble network is presented in FIG. 18. The proposed ensemble network was developed based on the bagging aggregating technique, an ensemble strategy to combine several sub-models and improve accuracy, see N. C. Oza, S. Russell, 2001, *Online bagging and boosting*, PMLR, 229-236. In a general bagging ensemble model, multiple sub-models will work individually and give their results. The final result will be determined by a majority vote. See, Id.

The proposed ensemble network contains two branches and four blocks. Branch 1 contains blocks 1-3. Branch 2 contains block 4. Each block is a homogeneous ensemble network composed of five sub-models with the same structures. Previous research has reported that CNN structures such as VGG, ResNet, and GoogLeNet work well on the fault diagnosis of bearing using vibration signals, see L. Wen, X. Li, X. Li, L. Gao, 2019, *A new transfer learning based on VGG-19 network for fault diagnosis*, IEEE, 205-209; Z. Ullah, B. A. Lodhi, J. Hur, 2020. *Detection and identification of demagnetization and bearing faults in PMSM using transfer learning-based VGG*, Energies 13 3834; G. Fan, J. Li, H. Hao, 2020. *Vibration signal denoising for structural health monitoring by residual convolutional neural networks*, Measurement 157 107651; G. Cao, K. Zhang, K. Zhou, H. Pan, Y. Xu, J. Liu, 2020, *A Feature Transferring Fault Diagnosis based on WPDR, FSWT and GoogLeNet*, IEEE, 1-6, and the identification of acoustic emission signals in the applications such as the monitoring of wear and bridge, see H. Xin, L. Cheng, R. Diender, M. Veljkovic, 2020. *Fracture acoustic emission signals identification of stay cables in bridge engineering application using deep transfer learning and wavelet analysis*, Advances in Bridge Engineering 1 1-16; F. König, G. Jacobs, A. Stratmann, D. Cornel, 2021, *Fault detection for sliding bearings using acoustic emission signals and machine learning methods*, IOP Publishing, 012013; and F. König, C. Sous, A. O. Chaib, G. Jacobs, 2021. *Machine learning based anomaly detection and classification of acoustic emission events for wear monitoring in sliding bearing systems*, Tribology International 155 106811. Therefore, the CNNs with ResNet-18, GoogLeNet, and VGG-19 structures are used as the sub-models in blocks 1-3 to obtain a good performance in the classification of AE signals. Random forest models are employed as machine learning sub-models in block 4. The proposed heterogeneous ensemble network model was named RGVF-HeteroESM-Net in this disclosure, in which RGVF consists of the first letters of ResNet-18 (R), GoogLeNet (G), VGG-19 (V), and random forest (F). RGVF-HeteroESM-Net is referred to as a heterogeneous ensemble network, which combines ResNet-18, GoogLeNet, VGG-19, and random forest models. The CWT image-based dataset is used as the input of blocks 1-3, and the AE feature-based dataset is utilized as the input for block 4. A bootstrapping, see S. Abney, 2002, *Bootstrapping*, 360-367, process is utilized to increase the diversity of each sub-model during the training. Each sub-model randomly selects 90% of samples from the training dataset as the true training data. All 20 sub-models were trained individually and tested on the test dataset. The final results were obtained through majority voting.

Block 1: VGG-19

VGG is developed based on the AlexNet model, see K. Simonyan, A. Zisserman, 2014. *Very deep convolutional networks for large-scale image recognition*, arXiv preprint arXiv: 1409.1556, which is a commonly used CNN structure. The number of layers was extended up to 19. The advantage of VGG-19 compared to AlexNet lies in replacing larger convolution kernels in AlexNet (11×11, 7×7, and 5×5 convolution kernels) by stacking 3×3 convolution kernels, see A. Krizhevsky et al. Using the stacked small convolution kernels, the number of layers and the nonlinearity of the network increases, which gives the network the ability to learn more complex features.

Figure 19:
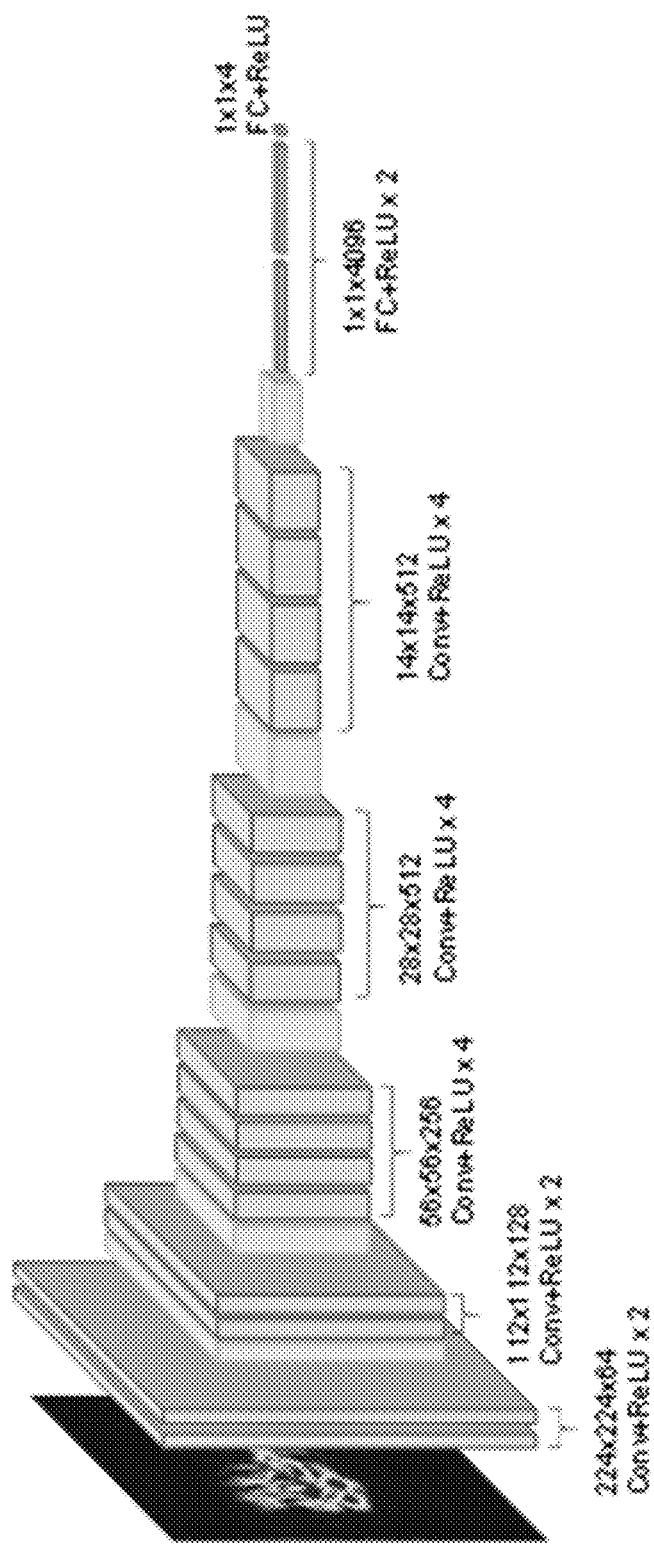
FIG. 19 shows one embodiment of a main structure of the modified VGG-19.

The VGG-19 structure is used in block 1 of the proposed ensemble network. The last FC layer of the VGG-19 structure is modified to have the class number consistent with the number of ASR phases. FIG. 19 shows the main structure of the modified VGG-19.

Block 2: GoogLeNet

Figure 20:
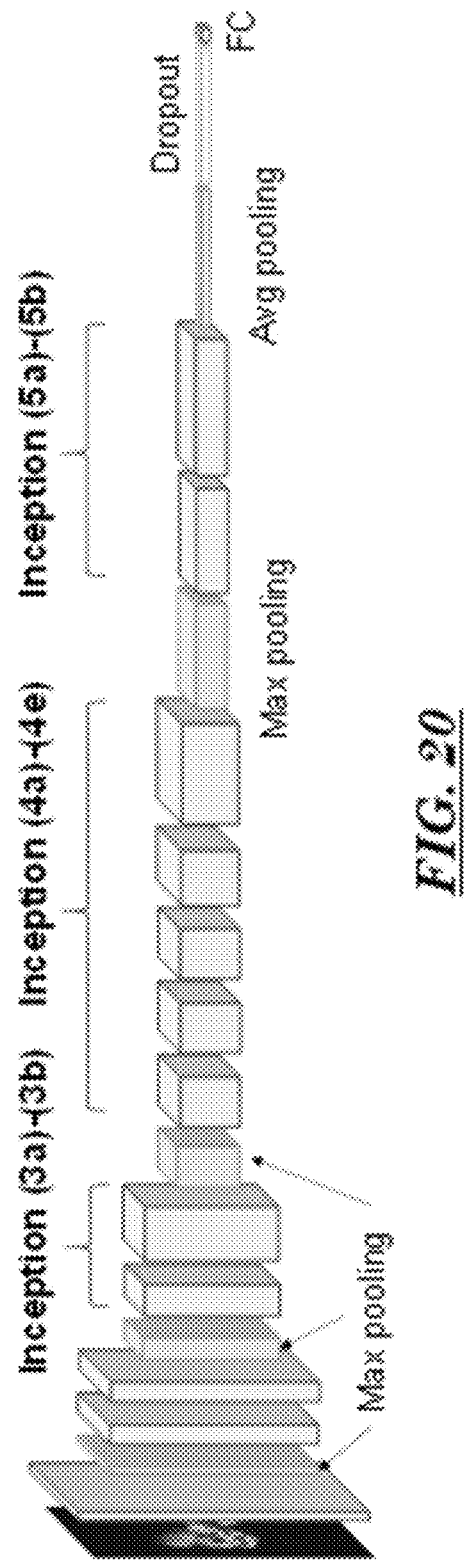
FIG. 20 shows one embodiment of a main structure of the modified GoogLeNet.

GoogLeNet is another improved model based on AlexNet. See, C. Szegedy, W. Liu, Y. Jia, P. Sermanet, S. Reed, D. Anguelov, D. Erhan, V. Vanhoucke, A. Rabinovich, 2015, *Going deeper with convolutions*, 1-9. The number of layers of GoogLeNet is extended up to 22. The innovation of GoogLeNet is the use of inception modules in the network. See, Id. Generally, in a layer of CNN, there is only one convolution kernel. However, the inception module uses multiple convolution kernels of different scales in a single layer. Therefore, some complex features in the images can be extracted by convolution kernels of different sizes. The feature extraction ability of each layer is thereby enhanced. GoogLeNet was utilized as the CNN structures in block 2 of the proposed ensemble network. Similar to the VGG-19 structure, the last FC layer of the GoogLeNet structure is modified. FIG. 20 shows the main structure of the modified GoogLeNet.

Block 3: ResNet-18

The ResNet-18 structure is a CNN structure with the idea of residuals. See, K. He, X. Zhang, S. Ren, J. Sun, 2016, Deep residual learning for image recognition, 770-778. Sometimes, the network's performance becomes less reliable when using a deeper structure due to gradient vanishing/explosion problems hindering network convergence. See, Id. A residual block module was developed and applied in the ResNet-18 structure to overcome this problem by introducing skip connections that enable gradients to flow across several layers. See, Id. The skip connections cause the outputs to learn a residual mapping.

Figure 21:
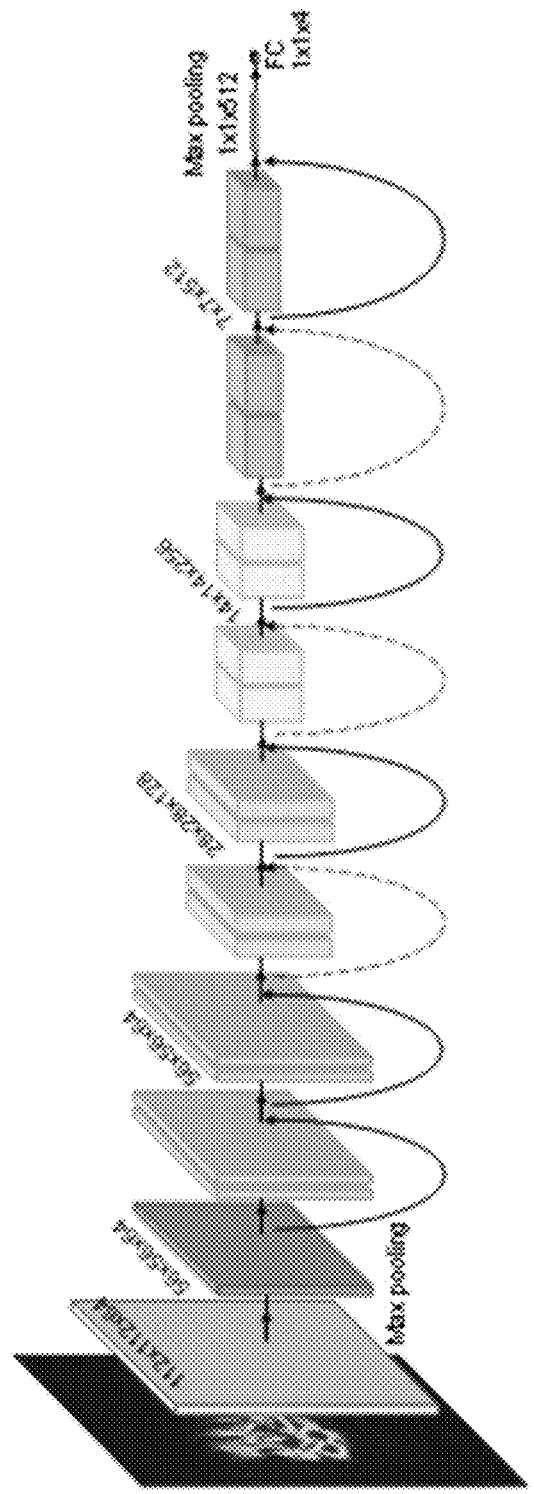
FIG. 21 shows one embodiment of a main structure of the modified ResNet-18.

In this disclosure, ResNet-18 was employed as one CNN structure in block 3 of the proposed ensemble network. As in the VGG-19 and GoogLeNet, the last FC layer is modified. FIG. 21 shows the main structure of the modified ResNet-18.

Block 4: Random Forest

Figure 22:
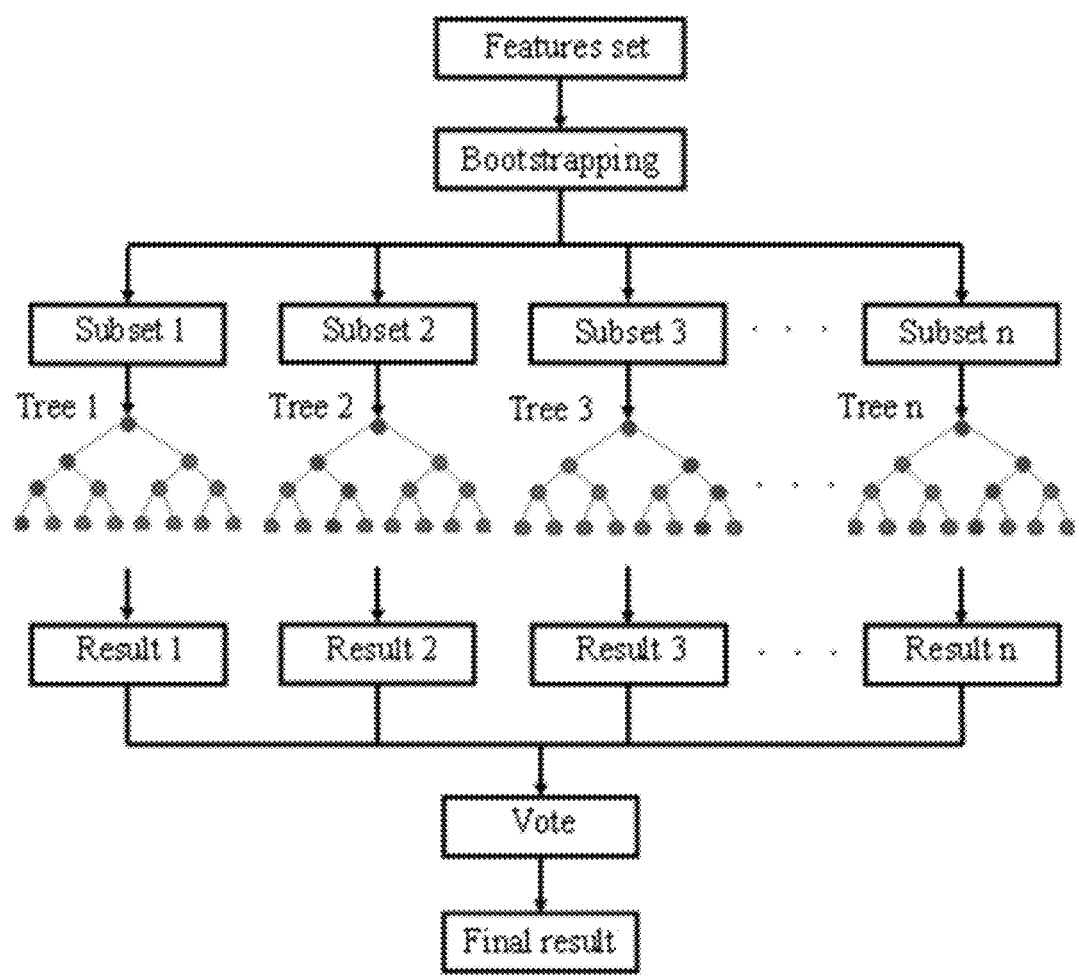
FIG. 22 shows one embodiment of a structure of a random forest.

Random forest is a machine learning model using a bagging algorithm. L. Breiman, 2001. *Random forests, Machine learning* 45 5-32. The sub-model inside the random forest is a decision tree. Bootstrapping, see Abney et al., is used to randomly selected data from the training dataset and create an input dataset for each decision tree. Some samples may be selected repeatedly, while some samples may not be selected. The data in the dataset that may not be chosen (even one time) is called out-of-bag (OOB) data, which can be used to test the generalization performance of the decision tree. See, L. Breiman, 1996. *Out-of-bag estimation*. The function of OOB data is similar to the validation dataset of a general machine learning method. Therefore, there is no need to have a specific validation dataset, and the data for the random forest is divided by training and testing data. The decision tree will derive the results individually after bootstrapping. The final result of the random forest is voted or averaged from all the results. The main structure of a random forest with n decision trees is presented in FIG. 22.

Results and Discussion

Analysis of AE Signals and ASR Phase Definition

During the ASR experiment, the AE signals were captured by ten AE sensors and recorded by the acquisition system. The data was filtered before conducting data analyses. A filtering procedure based on AE event definition was developed to remove extraneous data. An AE event refers to a set of AE hits captured by multiple AE sensors in a specific time interval. The time interval was defined based on the velocity of AE wave and the dimensions of the specimen. In this disclosure, the AE events recorded by at least four AE sensors were kept. The rest of the signals were considered as noise and were thereby removed. After filtering, 4413 AE signals remained for the analyses. As mentioned supra, each AE signal has 5120 data points. Therefore, the filtered AE dataset used in deep learning models is a matrix with a size of 5120×4413.

The amplitude of the filtered AE signals (shown as red dots) and the cumulative signal strength (CSS) are shown in FIG. 23. A rapid rise of CSS can be observed around 130 days. Two additional significant steps can be observed around 200 days and 350 days. The jumps in the CSS curve can be attributed to a fault developing in the specimen, herein crack formations or the propagation of existing cracks. The crack width was monthly measured for the surface cracks. The maximum crack widths were not necessarily attributed to the same crack and same location during the ASR process. The maximum crack widths in terms of time are illustrated in FIG. 23. A curve was also fitted to the crack width data, as seen in the figure. The first visual crack was observed at 146 days. The crack width expands rapidly from 0.06 mm at 146 days to 0.32 mm at 331 days. A crack with a width of 0.66 mm was observed at 438 days. Microscopic photos of cracks at 269, 331, and 438 days are also presented in FIG. 23. The magnification in the pictures is 184×. In addition to the crack width, expansion strains were measured monthly on the specimen surfaces. The volumetric strain refers to the accumulation of average strains along the X, Y, and Z axes. The fitted curve of the volumetric strain is also illustrated in FIG. 23. The fitted volumetric strain versus time and crack width versus time have a similar trend.

The development process of ASR in concrete can usually be divided into several phases, see Wallau et al. In this disclosure, the entire ASR process was divided into four phases, considering the crack widths, CSS trends, and the volumetric strains. The first phase is between 1-130 days, before the first rapid rise of CSS (microcrack phase). No visible cracks were observed during this phase on the concrete surfaces, and the volumetric strain ranged from 0% to 0.07%. The days between the first and the second significant steps of CSS (days 130-200) were defined as phase 2 (macrocrack initiation phase). In phase 2, the microcracks were merged and formed macrocracks. The first visible crack was observed in this phase, and the maximum crack width increased from 0 mm to 0.15 mm. The strain changed from 0.07% to 0.24% in phase 2. The days between the second and third steps of CSS (day 200-350) were defined as phase 3 (macrocrack extension and dilatation phase), where the crack width increased rapidly from 0.15 to 0.57 mm, and the strain changed from 0.24% to 0.74%. The last phase (between 350 to 460 days) was assigned to phase 4 (macrocrack rate decrease). In this phase, existing cracks were widened, but the rate of crack width widening was decreased. The maximum crack width increased from 0.57 mm to 0.69 mm in phase 4. The strain changed from 0.74% to 1%. This disclosure aims to automatically classify AE signals recorded during the ASR process according to the assigned phases (phase 1, phase 2, phase 3, and phase 4) by using the proposed heterogeneous ensemble learning framework.

Data Preparation

Feature-Based Dataset

The feature-based dataset served as the input of the random forest model. Twenty-five features (15 parametric features and 10 energy-frequency features) plus hit rate (introduced supra) were considered for the model.

Figure 25:
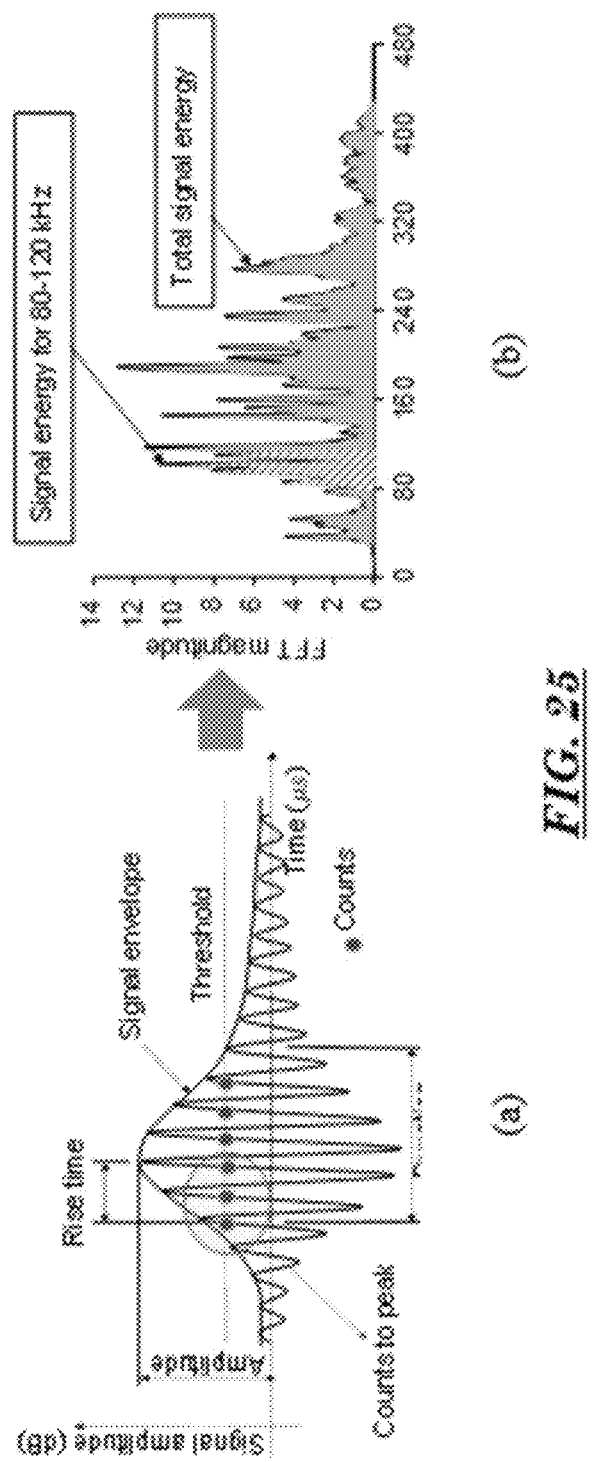
FIG. 25 shows extraction of energy-frequency features at: (a) AE time-domain waveform and some typical features; (b) energy-frequency features extraction procedure for 80-120 kHz.

AE parametric features are used to represent the specific characteristic of AE waveform. Some AE parametric features (amplitude, rise time, duration, counts to peak, counts) are shown in FIG. 25 at a. Definitions of parametric features are provided in Table 3, see FIG. 24.

The energy-frequency features refer to the energies in the frequency bands of the signals. The AE time domain waveforms were converted to the frequency domain spectrum by conducting a fast Fourier transform (FFT). The frequency range of the AE signals is 0-400 kHz and was divided into ten bands with a width of 40 kHz. The area under the FFT spectrum in each frequency band is the energy enclosed by that frequency band. See, Soltangharaei et al., Therefore, ten energy-frequency features could be derived from each AE signal. The procedure to extract the energy-frequency feature in the frequency band of 80-120 kHz is presented in FIG. 25 at b. The energies in the frequency bands were normalized to the total energy of the signal.

Image-Based Dataset

Figure 26:
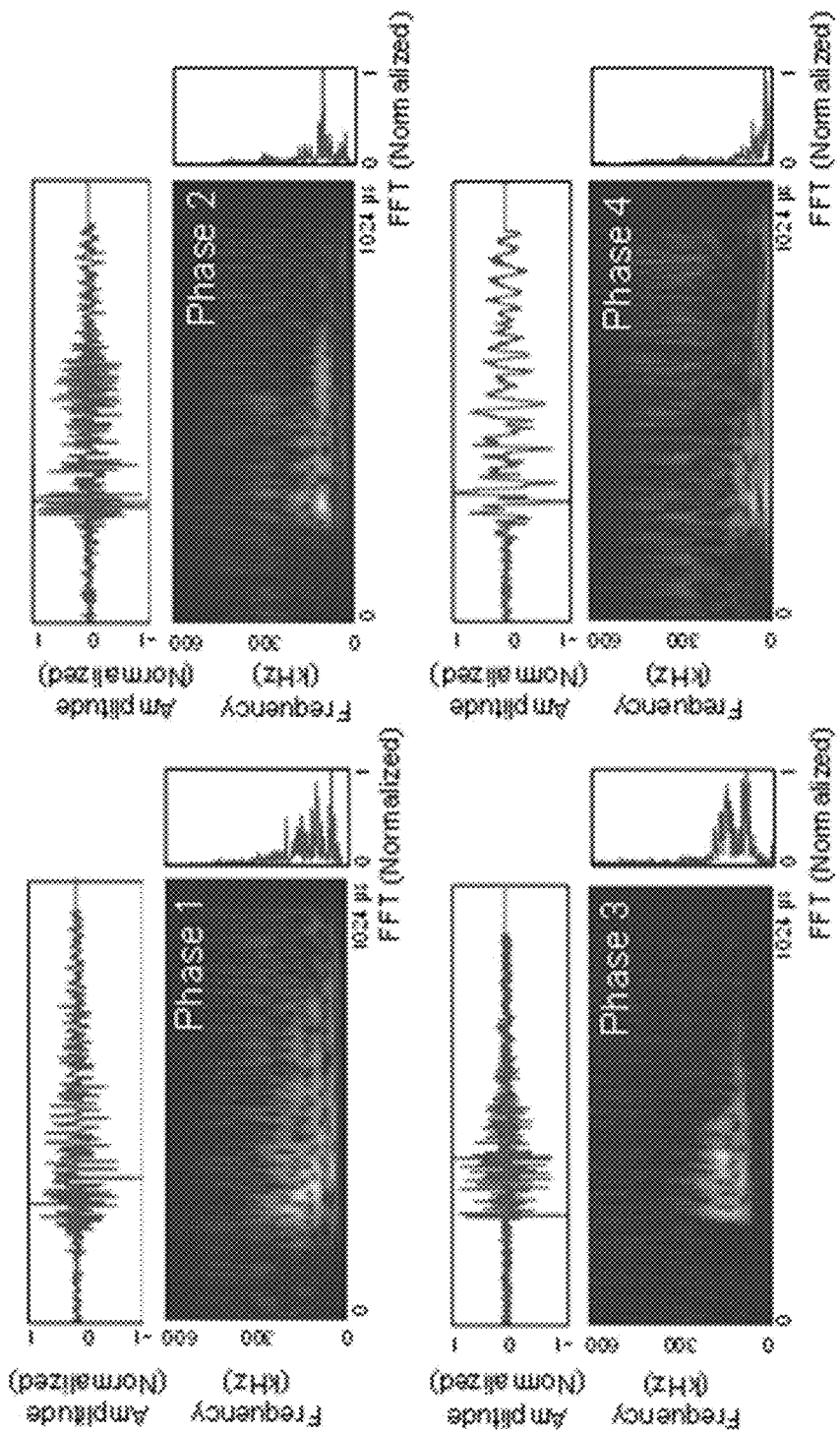
FIG. 26 shows CWT images of AE signals in phase 1 to 4.

All the recorded 4413 AE signals were transformed to CWT coefficients to form the image-based dataset. FIG. 26 illustrates example CWT images of signals for four phases. The amplitudes of time-domain waveforms were normalized from −1 to 1. The FFT spectra were normalized to a range of 0 to 1, and the wavelet coefficients were scaled between 0 to 1. The signals from different phases have different frequency contents, as seen in FIG. 26.

Figure 27:
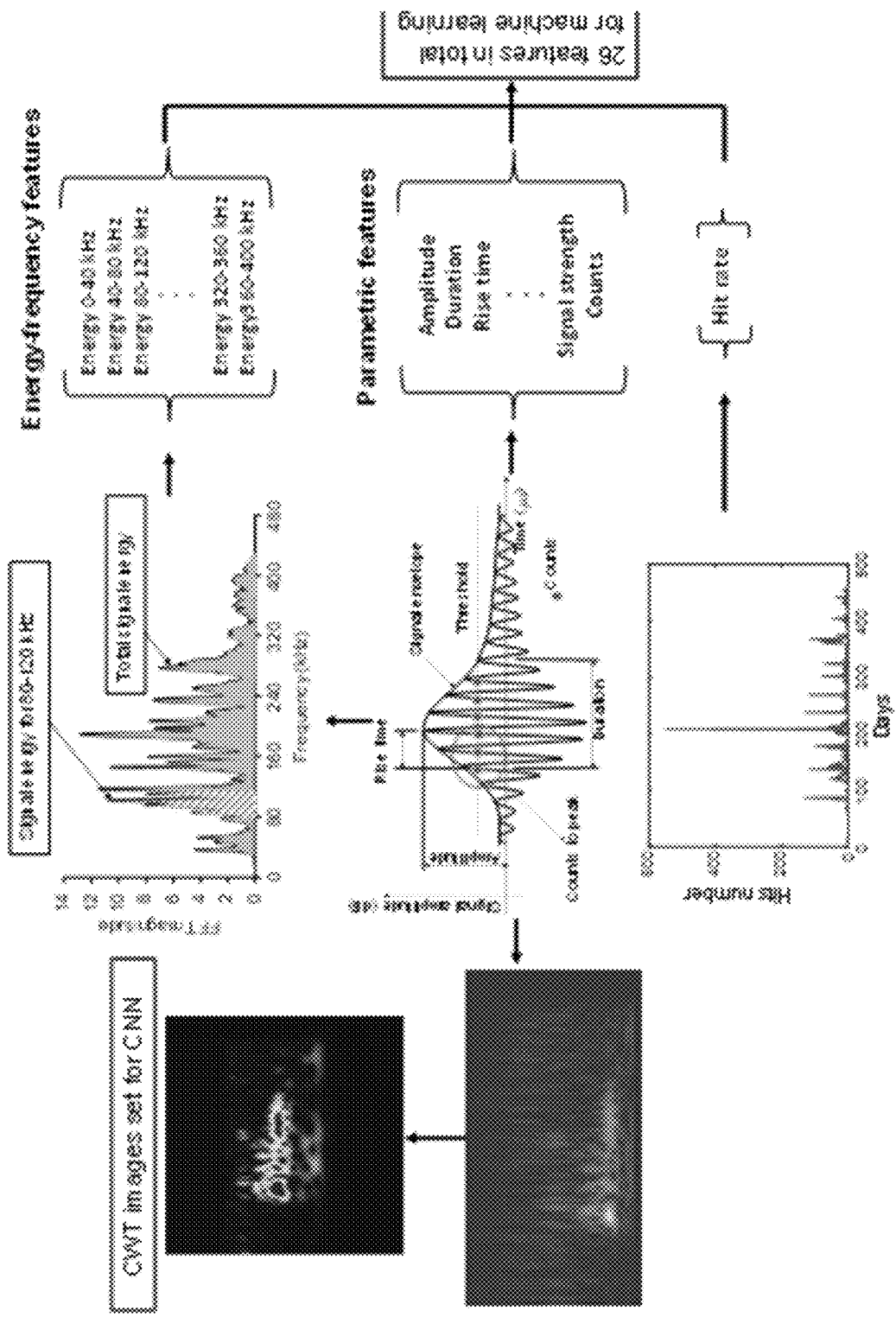
FIG. 27 shows an overview of one embodiment of the data preparation.

The overall procedures for the data preparation are shown in FIG. 27. AE parametric features were extracted from the original AE waveform. The energy-frequency features were extracted by the FFT spectrums, which were transformed from the waveforms. AE hit rate for each signal was calculated by the AE hit number recorded during the ASR experiment. The three parts (26 features) form the AE features-based dataset. In other words, the feature-based dataset has 4413 samples; each sample has 26 features. Furthermore, the AE waveforms were utilized to generate CWT coefficients. The Y-axis of the CWT coefficient was then converted to a logarithmic coordinate to present the time-frequency component more clearly. The coefficients were saved as RGB images with the size of 224×224×3 pixels. The CWT image-based dataset was composed of the derived RGB images and employed as the input of the CNN models.

ASR Evaluation Using Single CNN Model

Figure 28:
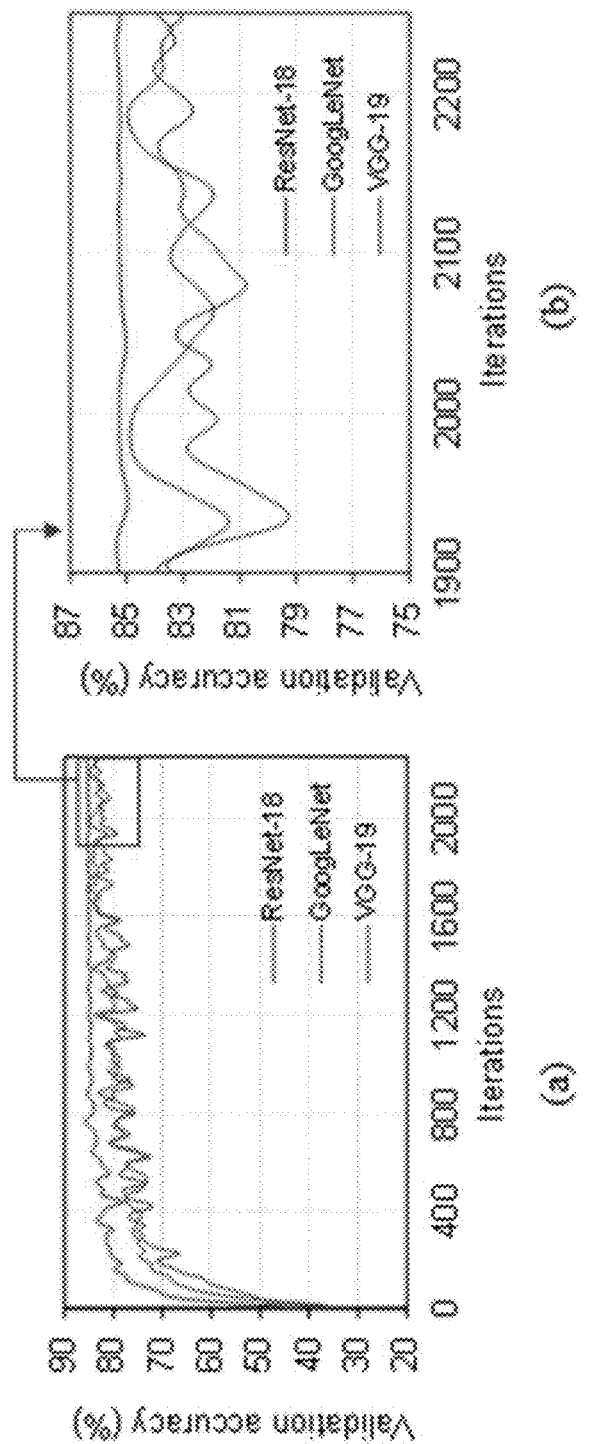
FIG. 28 shows validation accuracy curves at: (a) iteration 1-2250; (b) iteration 1900-2250.

The performance of ResNet-18, GoogLeNet, and VGG-19 models was evaluated. 80% of the image-based dataset (3531 images) was randomly selected as a training set. 10% of the image-based dataset (441 images) was randomly selected as a validation set. Finally, a test set was constructed by the remaining 10% (441 images) of the CWT images. The training, validating, and testing processes for the CNN models were conducted on a workstation with a CPU-Intel i7-6700 3.40 GHz, 32 GB RAM, and an Nvidia GPU-GTX1080. For all the CNN models, the gradient descent optimization was conducted using the Adaptive moment estimation (Adam) method. The optimized hyperparameters were set as follows: The minibatch size was 35, the learning rate was 0.0001, and the maximum number of epochs was 25. The three models were separately trained and tested by five trials. The bootstrapping process was applied to each CNN model. In each training process, 90% of the images (3178 images) were randomly selected from the training set as an input set to train the CNN models. The minibatch size was set as 35 so that there were 90 mini-batches in the input set. The maximum number of epochs was 25. In total, 2250 iterations were conducted. FIG. 28 at a presents the validation accuracy curves of the three models from iteration 1 to 2250. ResNet-18 converges faster (around iteration 400) than GoogLeNet and VGG-19 (around iteration 800), and the curve of ResNet-18 is more stable than the other two models after converging. The validation curves of different models are close to each other. FIG. 28 at b shows that ResNet-18 has the highest validation accuracy among the three models. However, the differences in validation accuracies between the models are not significant.

Testing accuracies of CNN models are presented in Table 4, see FIG. 29. The ResNet-18 model has the best performance. The average testing accuracy is 80.4% for VGG-19, 82.1% for GoogLeNet, and 82.8% for ResNet-18. The average accuracy for the three models ranges between 80%-83%, indicating the acceptable performance of models.

Figure 30:
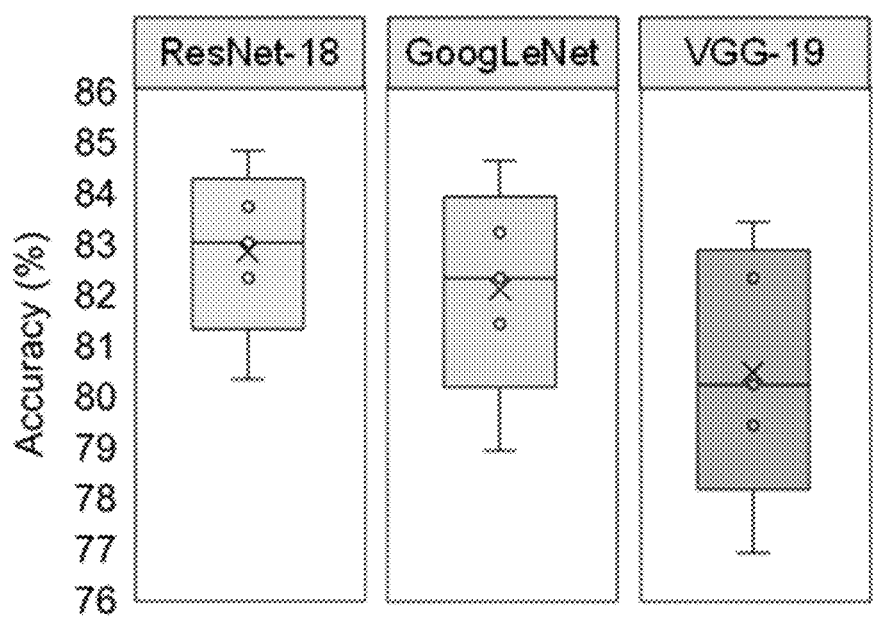
FIG. 30 shows a boxplot of the testing accuracies of the three CNN models.

The accuracy distributions of CNN models (ResNet-18, VGG-19, and GoogLeNet) were estimated by testing five trials for each model, as shown in FIG. 30. The boxes illustrate the interquartile ranges in the figure. The interquartile range describes the middle 50% of values when ranking from low to high. The VGG-19 model has the highest interquartile range, and ResNet-18 has the lowest interquartile range. The standard deviations of the testing accuracies were also calculated for three models: 0.168 for ResNet-18, 0.213 for GoogLeNet, and 0.254 for VGG-19. The ResNet-18 has the highest average testing accuracy, the lowest standard deviation. Therefore, it could be an optimal option among the models if a single CNN model is used to evaluate the ASR progression in concrete structures.

Figure 31:
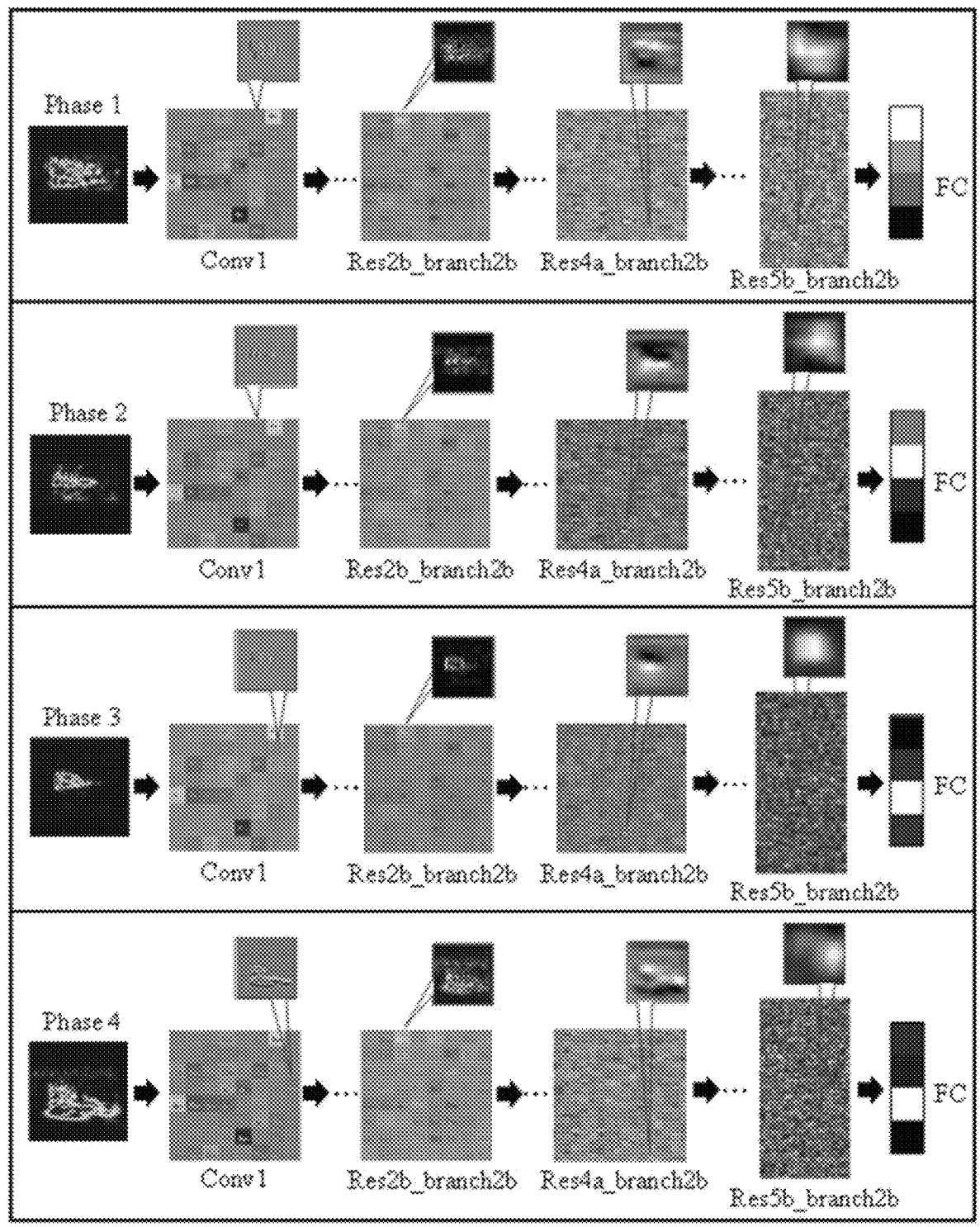
FIG. 31 shows visualization of feature extraction process of ResNet-18 in four phases.

The feature extraction process of ResNet-18 was visualized by showing the activations of feature maps in hidden layers when the testing accuracy was the highest (84.8%) among the five trials. In FIG. 31, the first convolutional layer (Conv1), two convolutional layers in the middle (Res2b_branch2b, and Res4a_branch2b), the last convolutional layer (Res5b_branch2b), and the last FC layer were selected to show the feature maps for the four ASR phases. Each feature map includes several smaller parts, named tiles in this disclosure, which are the output of different channels. The tiles with the strongest channel are zoomed and highlighted by red boxes in FIG. 31. White pixels in the feature map indicate strong positive activations. Black pixels are strong negative activations. The position of a pixel in the feature map corresponds to the same position in the input image. A white pixel at some locations in a channel indicates that the channel was strongly activated at that position. The first convolution layer learned basic features such as the outlines of the time-frequency components in the CWT images. More complicated features were learned in the deeper layers. The 4×1 vectors at the last FC layer show different color combinations for different phases. The vectors were transferred to a SoftMax layer for the classification.

Figure 32:
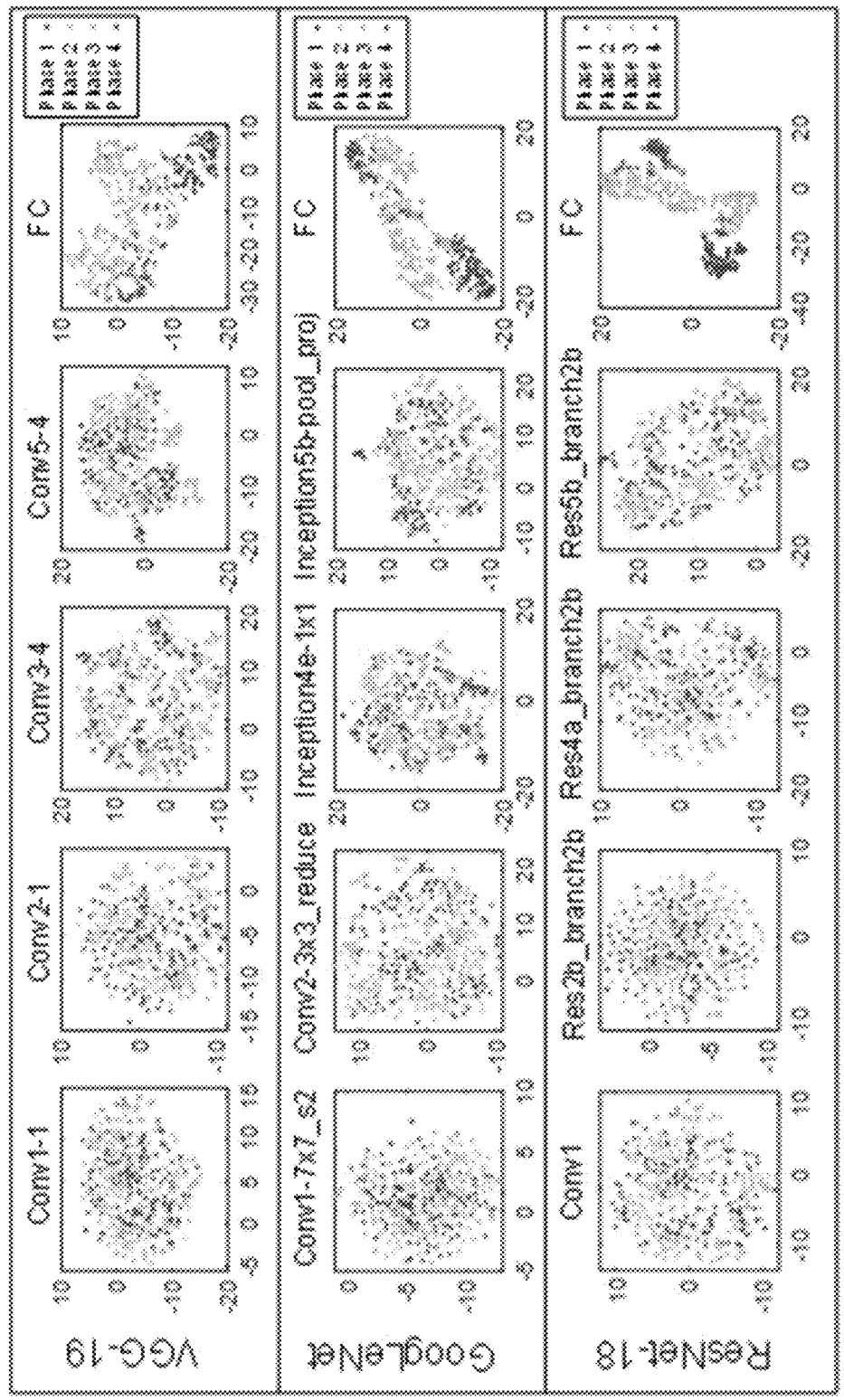
FIG. 32 shows visualization of the activation distribution through t-SNE.

There were 441 CWT images in the testing dataset. Therefore, 441 high-dimensional feature maps were generated by each layer. The feature maps were selected from the first convolutional layer, two convolutional layers in the middle, the last convolutional layer, and the last FC layer of the three CNN models. The selected feature maps were reduced to two dimensions by using t-distributed stochastic neighbor embedding (t-SNE). The t-distributed stochastic neighbor embedding (t-SNE) is an unsupervised dimension reducing technique that could embed high-dimensional data to a low-dimensional space to visualize the data in a Cartesian coordinates system. See, L. Van der Maaten, G. Hinton, 2008. *Visualizing data using t-SNE, Journal of machine learning research* 9. The reduced-dimensional data are presented in FIG. 32. Each data point in the figure is referred to as an embedding feature map dataset and was colored according to the corresponding ASR phase. In the first convolution layer, data points corresponding to four phases were scattered and mixed. The data points became more concentrated as the features were extracted in the deeper layers (shown from left to right in FIG. 32). Finally, the data points were divided into four classes (phases) in the last layer (FC layer). The scatter graphs are consistent with the testing accuracy results, as seen in FIG. 32. The four final clusters were clearly more separated for ResNet-18 model compared to the other models.

ASR Evaluation Using Single Random Forest Model

Figure 33:
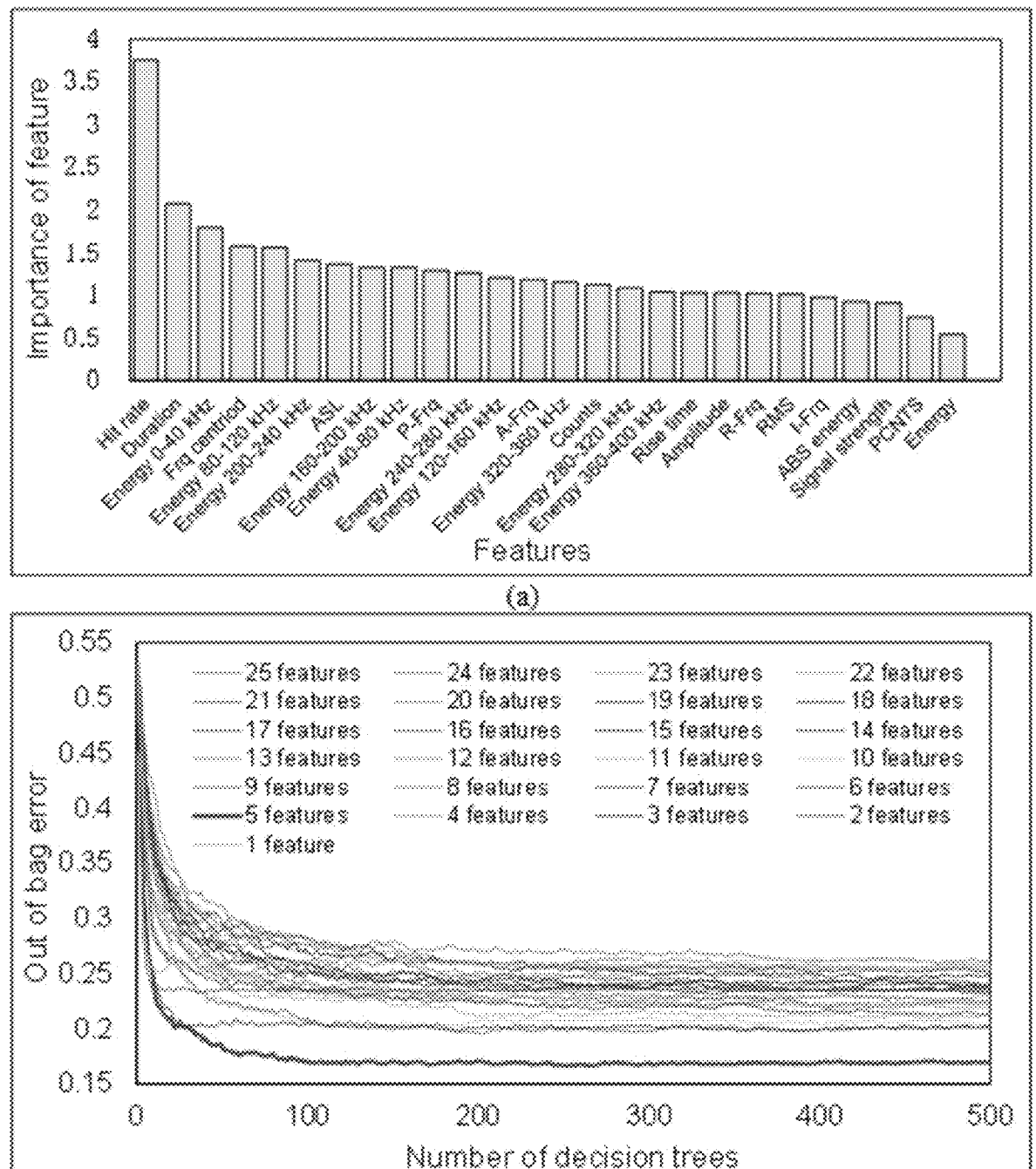
FIG. 33 shows evaluation of random forest at: (a) rank of features; and (b) OOB versus the number of decision trees.

The performance of the single random forest model was evaluated. The number of decision trees was initially set to 500. Testing data was 10% of the feature-based dataset (441 samples). The signal in the testing sets for both the random forest model and the CWT model were kept the same for the comparison purpose between the models. The remaining data (90% of the feature-based dataset, 3972 samples) were employed as the training set. The resulting OOB accuracy was 72.8%. The reason for the low accuracy might be due to some unrelated features among the 26 features. Therefore, a feature selection was employed to remove the unrelated features. One of the advantages of the random forest is that the importance of features can be calculated during the training, see L. Breiman, *Random Forests*. The rank of features according to the importance could thereby be obtained. FIG. 33 at a presents the rank of all the 26 features in the feature-based dataset. The importance of the features "Hit rate" is significantly higher than the rest, indicating the importance of the feature. The feature "Energy", and "PCNTs" hold the lowest importance. Based on the feature ranking, 25 subsets of features were created by using backward elimination. The number of features in the subsets varies from 1 to 25. For example, the subset with one feature has "Hit rate", the subset with two features has "Hit rate" and "Duration".

The optimum number of the decision tree was determined before evaluating the performance of the random forest model. FIG. 33 at b presents the OOB errors of all 25 subsets when the number of decision trees increases from 1 to 500. The OOB errors of all the models trained by the 25 subsets decrease rapidly when the number of trees increases. The errors remain almost constant as the number of decision trees increases to 200. Applying too many decision trees does not reduce the error but increases the computing time. Therefore, an appropriate number of decision trees was set as 200 in the final model.

Figure 34:
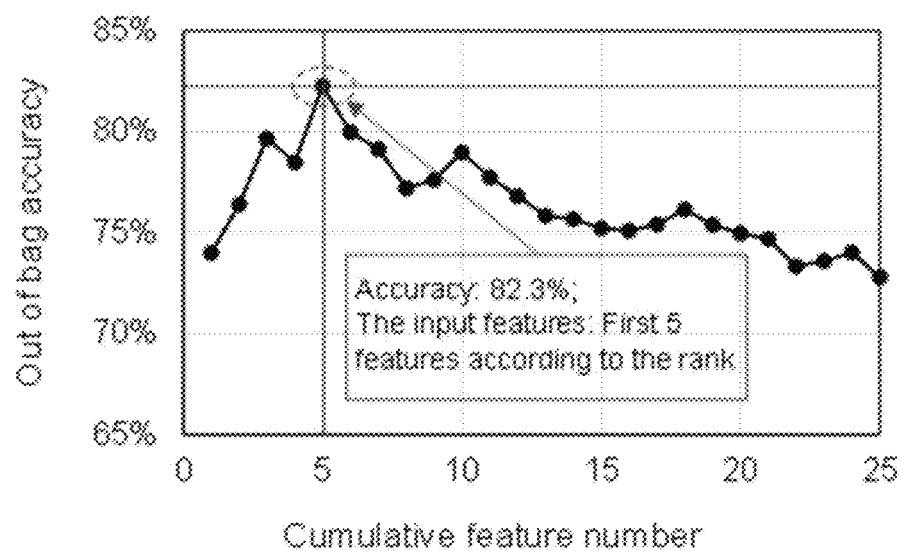
FIG. 34 shows testing results of random forest using 25 subsets.

The results of training are presented in FIG. 34. The highest OOB accuracy (82.3%) is obtained using the first five features. Therefore, the subset with "Hit rate", "Duration", "Energy 0-40 kHz", "Frequency centroid", and "Energy 80-120 kHz" was utilized as the selected features for the final model. A random forest with 200 decision trees was trained using the first five features. The model was employed to evaluate the performance in the testing set. The model was trained and tested with five trials. Bootstrapping was implemented before training, 90% of the samples (3178 samples) were randomly selected from the training set as the true input set to train the random forest model. The testing accuracies for the five trials were: 83.9%, 81%, 82.8%, 82.8%, and 84.1%. The average accuracy was 82.9%, and the standard deviation was 0.0123. The performance of this random forest model is close to ResNet-18. A lower standard deviation was observed because the random forest is a bagging ensemble algorithm that can decrease the standard deviation.

According to the rank of features, the hit rate has been proven to be a significant feature for the model to classify AE signals recorded during ASR. However, the hit rate of AE signals can only be calculated if the AE monitoring of concrete is not less than 24 hours. The accuracy of random forest with and without using the hit rate is presented in Table 5, see FIG. 35. The testing accuracy decreased from 82.9% to 50.3% when the hit rate was deleted from the features.

The two approaches have similar performance in the AE signal classification and can be used for the ASR evaluation. However, the random forest model with the hit rate feature has a limitation of 24-hours monitoring intervals contrary to the CNN models.

ASR Evaluation Using the Proposed Heterogeneous Ensemble Network

Figure 36:
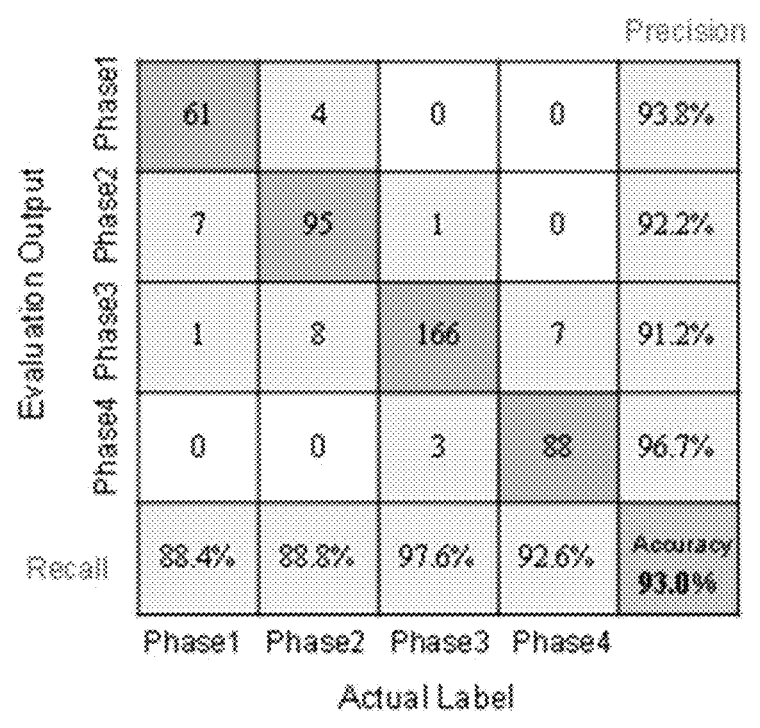

The performance of the proposed RGVF-HeteroESM-Net was evaluated. All 20 sub-models in blocks 1, 2, 3, and 4 work independently. As mentioned before, the diversity of the sub-models was ensured by applying the bootstrapping method. After training all models, the ensemble network was tested. The testing result is presented as a confusion matrix in FIG. 36. The overall accuracy was 93.0%. The number of AE signals correctly classified to their corresponding ASR phase is shown in the main diagonal of the matrix. Precision and recall rates are employed as parameters to evaluate the classification performance in each phase. Generally, the precision rate can be calculated by Eq. (7):

$$\text{Precision} = \frac{TP}{TP + FP} \quad (7)$$

where, TP, is the true positive, referring to the number of samples correctly classified to the attributed class. FP is the false positive, which refers to the number of samples that were misclassified into a class. The classification precision rate of phases 1 to 4 are 93.8%, 92.2%, 91.2%, and 96.7%, respectively.

The recall rate can be calculated as follow:

$$\text{Recall} = \frac{TP}{TP + FN} \quad (8)$$

The minimum AE monitoring time required for the RGVR-HeteroESM-Net is 24 hours because the random forest with the hit rate feature was included in the model. An additional heterogeneous ensemble network without random forest was created, and the performance was tested. This ensemble net was composed of five resNet-18, five GoogLeNet, and five VGG-19 models, which was named "RGV-HeteroESM-Net". The testing accuracy was 89.6% for this model (Table 6, see FIG. 37).

Four ensemble networks included: five ResNet-18 in block 3 (ResNet-18-ESM), five GoogLeNet in block 2 (GoogLeNet-ESM), five VGG-19 in block 1 (VGG-19-ESM), and five random forests in block 4 (RF-ESM) were also created and tested. Their testing accuracies were 87.5%, 86.2%, 84.4, and 85.3%, respectively (Table 5). The accuracies of the ensemble networks, the single CNN models, and the single random forest model are presented in Table 6, see FIG. 37. As seen in the table, the accuracies of ensemble networks are more than the corresponding single models, indicating the performance improvement of models using the heterogeneous ensemble strategy. The RGVF-HeteroESM-Net had the highest accuracy (93.0%) among the developed models.

Two shallow machine learning methods, SVM and KNN were also tested and compared with the models proposed. The accuracy results are also presented in Table 6, see FIG. 37. The input data of the machine learning models are the AE feature-based dataset (26 features). The RBF was selected as the kernel function of SVM. See, B. Scholkopf, K.-K. Sung, C. J. Burges, F. Girosi, P. Niyogi, T. Poggio, V. Vapnik, 1997. *Comparing support vector machines with Gaussian kernels to radial basis function classifiers*, IEEE transactions on Signal Processing 45 2758-2765. The optimized number of neighborhood "K" was set to 6 for the KNN model after several trials. The accuracy of SVM (63.7%) and KNN (57.1%) were much lower than the single models and the ensemble networks.

The high accuracy (93%) of the classification demonstrates that the proposed ensemble model can effectively distinguish the phases of ASR damage by using AE signals. This model is expected to apply to the concrete structures affected (or will be affected) by ASR. Several sensors are attached to the structure at the region with a higher risk of degradation, such as areas of the structure, as known to those of skill in the art, subject to fatigue, cracking, weathering, use induced faults, exposure to natural agents and/or moisture, shrinkage, corrosion in metals, loading degradation, chemical degradation, etc., and AE signals are acquired for a period of time. Then the signals are used as an input of the model, and the model is expected to determine the current ASR damage phase with relatively high reliability, although the model should be validated and improved for the data collected from the different specimens before field application. Computation time is also a point of great concern in practical applications. It determines whether a model is capable of running within a reasonable time frame. The computational times of all the models are also compared and presented in Table 6, see FIG. 37. The testing time in Table 6 refers to the time to classify a single signal in the test dataset. According to the results, the training times for the ensemble networks were higher than the single models. The training time for the CNN models (ResNet-18, GoogLeNet, VGG-19) is more than the training times for the machine learning models (random forest, SVM, KNN). Among the three CNN models, ResNet-18 has the lowest training time while VGG-19 has the highest. In the field application, the models will be trained offline with historical AE signals, and therefore, the training time will not be a primary concern. The classification of ASR phases in the field would be conducted based on the trained model, meaning that the testing time is the primary factor to be considered. The differences between times for the trained models to classify a single AE signal are negligible. All the trained models can finish the classification within 1 second. Therefore, considering the accuracy and computational time, the RGVF-HeteroESM-Net had the highest accuracy (93.0%) and an acceptable testing time (0.97 seconds).

SUMMARY AND CONCLUSIONS

This disclosure proposes a temporal ASR evaluation method based on AE monitoring and an ensemble learning framework. A concrete block with reactive aggregates was used as an experimental specimen. The ASR process was accelerated by providing high temperature and humidity in the chamber. The ASR expansion was measured using DEMEC gauge on a regular basis, and the crack width was measured by a Dino-Lite digital microscope. The AE data were continuously acquired for 460 days and were divided into four phases, defined in terms of time. Two types of input datasets, including the CWT images and AE features, were created based on the recorded AE signals. A heterogeneous ensemble learning network composed of ResNet-18, GoogLeNet, VGG-19, and random forest was developed to classify the data into the ASR phases with high accuracy. The proposed methodology showed an acceptable classification performance and computational time on the testing dataset. This indicates that the ASR damage phase can be potentially determined for the concrete structures in the field. The main conclusions of this disclosure are summarized as follows:

The classification performance of single models such as ResNet-18, GoogLeNet, VGG-19, and random forest were tested. The results depicted that ResNet-18 and the random forest model were more accurate than other models.

The hit rate is an important feature to be considered in the machine learning methods for the ASR AE data. However, this feature was calculated based on a monitoring time not less than 24 hours. Low classification accuracy was obtained when the random forest model was trained without the hit rate.

The classification performance of the ensemble networks in this disclosure was investigated. The results suggest that the ensemble networks are more accurate than the single models. Among all the ensemble networks, RGVF-HeteroESM-Net has the best performance.

Effect of source/sensor distance on the AE model result can be a potential future work to improve the model. The propagation distance between the sources and the sensor is not always the same, which can influence the frequency content and other signal features. E. Maillet, C. Baker, G. N. Morscher, V. V. Pujar, J. R. Lemanski, 2015. *Feasibility and limitations of damage identification in composite materials using acoustic emission, Composites Part A: Applied Science and Manufacturing* 75 77-83; and A. Farhidzadeh, A. C. Mpalaskas, T. E. Matikas, H. Farhidzadeh, D. G. Aggelis, 2014. *Fracture mode identification in cementitious materials using supervised pattern recognition of acoustic emission features, Construction and building materials* 67 129-138. This can be more significant when the developed method is used for large-scale structures. One of the challenges in the application of the proposed method in the field can be the result generalization. Future research should focus on the study of the result generalization by testing the trained model on different concrete specimens such as specimens with different or same materials and boundary conditions.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

What is claimed is:

1. An acoustic emission method for monitoring structural health of concrete comprising:
    affixing at least one acoustic emission sensor to a concrete structure;
    obtaining at least one acoustic emission waveform from the concrete structure;
    employing at least one deep learning algorithm to analyze the at least one acoustic emission waveform to determine a condition of the concrete structure with respect to at least one Alkali-silica reaction progress wherein the at least one deep learning algorithm attributes the Alkali-silica reaction process to an Alkali-silica expansion range and an Alkali-silica reaction damage phase is determined for the concrete structure based on the at least one acoustic emission waveform from the concrete structure;

wherein the at least one deep learning algorithm includes at least one convolutional neural network and at least one stacked autoencoder:

wherein at least one heterogeneous ensemble learning network, including the at least one convolutional neural network, and at least one random forest classifies the Alkali-silica reaction damage phase; and wherein the method is nondestructive to the concrete structure being monitored.

2. The acoustic emission method of claim 1, further comprising converting the at least one acoustic emission waveform to at least one continuous wavelet transform image.

3. The acoustic emission method of claim 1, further comprising obtaining at least one feature based dataset by extracting at least one parametric feature from the at least one acoustic emission waveform.

4. The acoustic emission method of claim 2, wherein the continuous wavelet transform is expressed as $$CWT_{(a,b)} = \frac{1}{\sqrt{|a|}} \int_{-\infty}^{\infty} x(t)\psi^*\left(\frac{t-b}{a}\right)dt.$$

5. The acoustic emission method of claim 1, further comprising forming the at least one convolutional neural network to include multiple convolution kernels.

6. The acoustic emission method of claim 5, further comprising forming the multiple convolution kernels to vary in size from one another.

7. The acoustic emission method of claim 1, further comprising detecting a fault in the concrete structure via an increase in cumulative signal strength.

8. The acoustic emission method of claim 1, further comprising affixing the at least one sensor to an area of the concrete structure subject to degradation.

9. The acoustic emission method of claim 1, further comprising wherein the heterogeneous ensemble network model comprises ResNet-18, GoogLeNet, VGG-19, and random forest.

10. A system for monitoring structural health of concrete comprising:
at least one acoustic emission sensor affixed to a concrete structure for obtaining at least one acoustic emission waveform from the concrete structure;
at least one deep learning algorithm learning framework to analyze the at least one acoustic emission waveform to determine a condition of the concrete structure with respect to at least one Alkali-silica reaction progress wherein the at least one deep learning algorithm learning framework attributes the Alkali-silica reaction process to an Alkali-silica expansion range and an Alkali-silica reaction damage phase is determined for the concrete structure based on the at least one acoustic emission waveform from the concrete structure;

wherein the at least one deep learning algorithm includes at least one convolutional neural network and at least one stacked autoencoder;

wherein at least one heterogeneous ensemble learning network, including the at least one convolutional neural network, and at least one random forest classifies the Alkali-silica reaction damage phase; and wherein the system is nondestructive to the concrete structure being monitored.

11. The system for monitoring structural health of claim 10, further comprising converting the at least one acoustic emission waveform to at least one continuous wavelet transform image.

12. The system for monitoring structural health of claim 10, further comprising obtaining at least one feature based dataset by extracting at least one parametric feature from the at least one acoustic emission waveform.

13. The system for monitoring structural health of claim 11, wherein the continuous wavelet transform is expressed as $$CWT_{(a,b)} = \frac{1}{\sqrt{|a|}} \int_{-\infty}^{\infty} x(t)\psi^*\left(\frac{t-b}{a}\right)dt.$$

14. The system for monitoring structural health of claim 10, wherein the at least one convolutional neural network comprising multiple convolution kernels.

15. The system for monitoring structural health of claim 14, wherein the multiple convolution kernels vary in size from one another.

16. The system for monitoring structural health of claim 10, further comprising detecting a fault in the concrete structure via an increase in cumulative signal strength acquired by the at least one acoustic emission sensor.

17. The system for monitoring structural health of claim 10, wherein the at least one sensor is affixed to an area of the concrete structure subject to degradation.

18. The system for monitoring structural health of claim 10, further comprising wherein the heterogeneous ensemble network model comprises ResNet-18, GoogLeNet, VGG-19, and random forest.

* * * * *